(12) United States Patent
Boothman et al.

(10) Patent No.: US 6,890,950 B2
(45) Date of Patent: May 10, 2005

(54) LAPACHONE DELIVERY SYSTEMS, COMPOSITIONS AND USES RELATED THERETO

(75) Inventors: David Boothman, Sagamore Hills, OH (US); Jinming Gao, Pepper Pike, OH (US); Norased Nasongkla, Cleveland, OH (US); John Pink, Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 43 days.

(21) Appl. No.: 10/422,053

(22) Filed: Apr. 23, 2003

(65) Prior Publication Data

US 2004/0001871 A1 Jan. 1, 2004

Related U.S. Application Data

(60) Provisional application No. 60/374,693, filed on Apr. 23, 2002.

(51) Int. Cl.[7] ..................... A61K 31/352; C07D 311/92
(52) U.S. Cl. ........................ 514/454; 514/455; 549/389
(58) Field of Search ........................ 549/389; 514/454, 514/455

(56) References Cited

U.S. PATENT DOCUMENTS

| 5,100,669 A | * | 3/1992 | Hyon et al. ................ 424/426 |
| 2003/0091639 A1 | * | 5/2003 | Jiang et al. ................ 424/486 |

FOREIGN PATENT DOCUMENTS

| WO | WO- 94 04145 | 3/1997 |
| WO | WO- 97 07797 | 3/1997 |
| WO | WO- 97 08162 | 3/1997 |
| WO | WO- 97 31936 | 9/1997 |
| WO | WO- 00 61142 | 10/2000 |
| WO | WO- 02 058694 | 8/2002 |
| WO | WO- 03 011224 | 2/2003 |

* cited by examiner

*Primary Examiner*—Taofiq Solola
(74) *Attorney, Agent, or Firm*—Ropes & Gray LLP

(57) ABSTRACT

In part, the present invention is directed to a system comprising a lapachone or a prodrug thereof and a polymer, such as a biocompatible and optionally biodegradable polymer, methods for treatment using the subject polymer compositions, and methods of making and using the same. In another part, the present invention includes inclusion complexes of a lapachone or a prodrug thereof and a cyclodextrin, preferably a β-cyclodextrin, such as hydroxypropyl β-cyclodextrin, e.g., to improve the solubility of the lapachone or prodrug thereof.

20 Claims, 15 Drawing Sheets

LAPACHONE DELIVERY SYSTEMS, COMPOSITIONS AND USES RELATED THERETO

RELATED APPLICATION

This application claims the benefit of, and incorporates by reference, the entire disclosure of U.S. Provisional Patent Application No. 60/374,693, filed Apr. 23, 2002.

BACKGROUND OF THE INVENTION

β-Lapachone (β-lap) is a potent cytotoxic agent that demonstrates antitumor activity against a variety of human cancer cells at concentrations typically in the range of 1–10 μM ($IC_{50}$). The drug was first isolated from the bark of the Lapacho tree (genus Tabebuia) in the rainforests of South America, which has a long history as an herbal medicine. Cytotoxicity has been demonstrated in transformed cell lines derived from patients with promyelocytic leukemia, prostate, malignant glioma, hepatoma, colon, breast, ovarian, pancreatic, and multiple myeloma cell lines including drug-resistant lines (Planchon et al., Cancer Res., 55 (1996) 3706; Li, C. J., et al., Cancer Res., 55 (1995) 3712; Weller, M. et al., Int. J Cancer, 73 (1997) 707; Lai, C. C., et al. Histol Histopathol, 13 (I 998) 8; Huang, L., et al., Mol Med, 5, (1999) 711; Wuertzberger, S. M., et al., Cancer Res., 58 (1998) 1876; Li, C. J. et al., Proc. Natl. Acad Sci. USA; 96(23) (1999) 13369–74; Li, Y., et al., Mol Med, 6 (2000) 1008; and Li, Y. Z., Mol Med, 5 (1999) 232). No cytotoxic effects were observed on normal fresh or proliferating human PBMC (Li, Y., et al., Mol Med, 6 (2000) 1008).

β-Lapachone and its derivatives have also been synthesized and tested as anti-viral and anti-parasitic agents (Goncalves, A. M., et al. . Mol. Biochem. Parasitology, I (1980) 167–176; Schaffner-Sabba, K., et al., J Med, Chem., 27 (1984) 990–994).

β-Lapachone has been shown to be a DNA repair inhibitor that sensitizes cells to DNA-damaging agents including radiation (Boothman, D. A. et al., Cancer Res, 47 (1987) 5361; Boorstein, R. J., et al., Biochem. Biophys. Commun., 117 (1983) 30). β-Lapachone has been asserted to have potent in vitro inhibition of human DNA Topoisomerases I (Li, C. J., et al., J Biol. Chem., 268 (1993) 22463) and II (Frydman, B. et al., Cancer Res. 57 (1997) 620) with novel mechanisms of action. Topoisomerase I is an enzyme that unwinds the DNA that makes up the chromosomes. The chromosomes must be unwound in order for the cell to use the genetic information to synthesize proteins; β-lapachone may keep the chromosomes wound tight, so that the cell cannot make proteins. As a result, the cell stops growing. Because cancer cells are constantly replicating and circumvent many mechanisms that restrict replication in normal cells, they are more vulnerable to topoisomerase inhibition than are normal cells.

Another possible intracellular target for β-lapachone in tumor cells is the enzyme NAD(P)H:quinone oxidoreductase (NQO1, E.C. 1.6.99.2). β-lapachone is bioactivated by the NQO1 enzyme, which is a ubiquitous flavoprotein found in most eukaryotic cells. This enzyme catalyzes a two-electron reduction of various quinones, utilizing either NADH or NADPH as electron donors. Biochemical studies suggest that reduction of β-lapachone by NQO1 leads to a "futile cycling" between the quinone and hydroquinone forms with a concomitant loss of reduced NADH or NAD (P)H (Pink, J. J. et al, J Biol Chem., 275 (2000) 5416). The exhaustion of these reduced enzyme cofactors may be a critical factor for the activation of the apoptotic pathway after β-lapachone treatment. The human NQO1 gene encodes a 30 kDa protein that is expressed in a tissue-dependent manner. More importantly, NQO1 is over-expressed (up to 20-fold) in a number of tumors, including breast, colon and lung cancers, compared with adjacent normal tissue (1–4). Over-expression of NQO1 in cancerous cells makes it an ideal target for tumor-selective drug therapies with minimal toxicities to healthy cells.

Despite the potency and selectivity of β-lap in killing cancer cells in vitro, the low water solubility of β-lapachone (0.04 mg/ml or 0.16 mM) limits its potential for systemic administration and clinical applications in vivo. β-lapachone is highly insoluble in water and has only limited solubility in common solvent systems used for topical and parenteral administration. As a result, there is a need for improved formulations of β-lapachone for therapeutic purposes that are both safe and readily bioavailable to the subject to which the formulation is administered.

SUMMARY OF THE INVENTION

In part, the present invention is directed to a system comprising a lapachone or a prodrug thereof and a polymer, such as a biocompatible and optionally biodegradable polymer, methods for treatment using the subject polymer compositions, and methods of making and using the same. In another part, the present invention includes inclusion complexes of a lapachone or a prodrug thereof and a cyclodextrin, preferably a β-cyclodextrin, e.g., a hydroxy-alkyl cyclodextrin such as hydroxypropyl β-cyclodextrin, e.g., to improve the solubility or bioavailability of the lapachone.

Lapachones are known to have activity against neoplastic cells, as described in U.S. Pat. Nos. 5,969,163, 5,824,700, and 5,763,625. Antiviral activity (in combination with xanthine) or reverse transcriptase inhibitory activity for lapachones is suggested in U.S. Pat. Nos. 5,641,773 and 4,898,870, while antifungal and trypanosidal activity of lapachones is suggested in U.S. Pat. Nos. 5,985,331 and 5,912,241. Accordingly, it is contemplated that the subject compositions will be useful as antimalarial, antifungal, antiparasitic, and/or antiviral therapeutics. Additional discussion of uses for lapachones can be found in U.S. patent applications Ser. Nos. 2,003,064,913, 2,003,036,515, 2,003, 013,677, and 20,030,169,135, and U.S. Pat. No. 6,245,807.

Thus, in one embodiment, the invention provides a lapachone or a prodrug thereof, such as described herein, e.g., having a structure of Formula I or II, complexed with a β-cyclodextrin, e.g., a hydroxyalkyl cyclodextrin such as hydroxypropyl β-cyclodextrin. The complex, preferably an inclusion complex, may be combined with a pharmaceutically acceptable excipient to provide a pharmaceutical formulation, e.g., suitable for administration to a patient, that may be useful as an antimalarial, antifungal, antiparasitic, and/or antiviral therapeutic.

In another aspect, the invention provides a drug delivery system, comprising a lapachone or a prodrug thereof as described herein, such as a lapachone of Formula I or II, incorporated in a biocompatible polymer. In certain embodiments, the lapachone is admixed with the polymer, although the lapachone may be coated with the polymer, or may otherwise be placed in contact with the polymer. The system may be an implant, such as a millirod dimensioned to position two radiation seeds a predetermined distance apart, or may be microparticles and/or nanoparticles, such as microspheres and/or nanospheres. In certain embodiments, the lapachone is provided as an inclusion complex with hydroxypropyl cyclodextrin. The polymer may include one or more of poly(lactic-co-glycolic acid) (PLGA), poly(lactic acid) (PLA), polyethylene glycol (PEG), polysebacic acid (PSA), or a polyanhydride, or copolymers of any of these. In certain embodiments, a diagnostic agent, an imaging agent, or an adjuvant is also incorporated in the polymer.

In one aspect, the subject polymers may be biocompatible, biodegradable or both. The polymers comprise monomeric units arranged to form polymers as described in detail below. In the subject polymers, the chemical structure of certain of the monomeric units may be varied to achieve a variety of desirable physical or chemical characteristics, including, for example, release profiles, or handling characteristics of the resulting polymer composition.

In certain embodiments, one or more additional biologically active agents may be encapsulated by the subject polymer. In certain embodiments, such agents may include compounds that counteract side effects induced by the lapachone, such as dicoumarol, while in other embodiments, such agents may include compounds that enhance or augment the desired effects of the lapachone. In certain embodiments, the subject polymers are combined with one or more other materials that alter the physical/or and chemical properties of the resulting polymer, including, for example, the release profile of the resulting polymer composition for an incorporated biologically active agent. Examples of such materials include biocompatible plasticizers, delivery agents, fillers, and the like.

In certain embodiments, the subject compositions are in the form of microspheres. In other embodiments, the subject compositions are in the form of nanospheres. In one embodiment, the microspheres or the nanospheres are formed in an emulsion. In another embodiment, the subject compositions of the present invention may be lyophilized or subjected to another appropriate drying technique such as spray drying and subsequently used directly, e.g., inhaled or injected as powder using an appropriate powder inhalation or injecting device, or rehydrated before use.

In another aspect, the present invention is directed to methods of using the subject polymer compositions for prophylactic or therapeutic treatment. In certain instances, the subject compositions may be used to prevent or treat a disease or condition in an animal, such as a human. In certain embodiments, use of the subject compositions that release in a sustained manner a therapeutic agent allow for different treatment regimens than are possible with other modes of administration of such therapeutic agent.

In another aspect, the efficacy of treatment using the subject compositions may be compared to treatment regimens known in the art in which a therapeutic and/or biologically active agent is not encapsulated with a subject polymer, e.g., the agent is combined with a different polymer, or is administered substantially free of a polymer. Agents that may be encapsulated in the subject compositions include imaging and diagnostic agents (such as radioopaque agents, labeled antibodies, labeled nucleic acid probes, dyes, such as colored or fluorescent dyes, etc.) and adjuvants (radiosensitizers, transfection-enhancing agents (such as chloroquine and analogs thereof), chemotactic agents and chemoattractants, peptides that modulate cell adhesion and/or cell mobility, cell permeabilizing agents, inhibitors of multidrug resistance and/or efflux pumps, etc.).

In another aspect, the subject polymers may be used in the manufacture of a medicament for any number of uses including, for example, treating any disease or other treatable condition of a patient. In still other aspects, the present invention is directed to a method for formulating polymers and compositions of the present invention in a pharmaceutically acceptable carrier.

In other embodiments, this invention contemplates a kit including subject compositions, and optionally instructions for their use. Uses for such kits include, for example, therapeutic applications. In certain embodiments, the subject compositions contained in any kit have been lyophilized and/or spray dried and may require rehydration before use. For example, in one embodiment, the invention provides a kit comprising a lapachone or a prodrug thereof as described herein, such as a lapachone of Formula I or II, a β-cyclodextrin (optionally a hydroxyalkyl cyclodextrin, such as hydroxypropyl β-cyclodextrin, and instructions for combining the lapachone and β-cyclodextrin to form a complex and administering the complex to a patient In certain embodiments, microparticles of the invention may be packed in an inhaler for pulmonary delivery, e.g., for delivery locally to the lungs or for systemic delivery through the lungs and/or nasal passages.

In another aspect, the invention provides a method of inhibiting proliferation of a cancerous cell in a patient by administering to the patient a composition as described herein. In certain embodiments, the cell overexpresses NQO1. In certain embodiments, the cell is a lung cancer cell (such as a non-small cell lung cancer cell), a breast cancer cell, or a prostate cancer cell. In certain embodiments, the composition is delivered to the patient by inhalation of microspheres comprising a lapachone or a prodrug thereof and a biocompatible polymer, e.g., to treat lung cancer or deliver the lapachone systemically. In certain embodiments, the cell is a prostate cancer cell and the system is delivered to the patient by implanting radioactive seeds spaced apart by at least one polymeric millirod comprising a lapachone or a prodrug thereof and a biocompatible polymer.

These embodiments of the present invention, other embodiments, and their features and characteristics will be apparent from the description, drawings, and claims that follow.

DETAILED DESCRIPTION OF THE INVENTION

1. Overview

Figure 1:
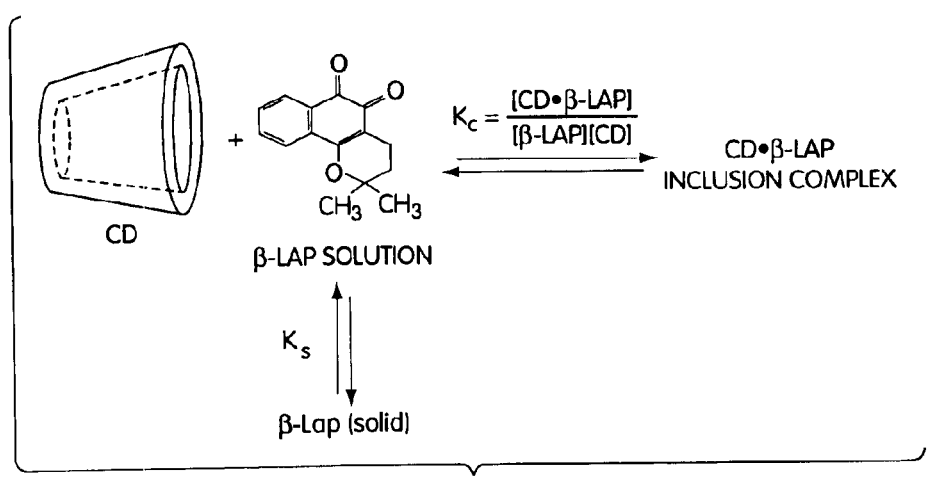
FIG. 1. Schematic diagram of the solubility equilibriums of β-lap in aqueous solutions containing cyclodextrin (CD). $K_s$ and $K_c$ are the equilibrium constants for β-lap solubility and formation of inclusion complex, respectively. [CD-β-lap], [β-Lap] and [CD] are the concentrations of CD-β-lap complex, free β-lap and free CD, respectively.

The present invention relates to strategies for the delivery of a lapachone or a prodrug thereof to a patient in need thereof, including sustained release delivery, through a wide variety of routes, including microspheres and nanospheres for injection or inhalation. The polymers can be prepared using clinically approved monomers, including lactic acid (LA), glycolic acid (GA), sebacic acid (SA), 1,3-bis (carboxyphenoxy)propane (CPP), and blocks of poly(lactic-co-glycolic acid)(PLGA) and/or poly(ethylene glycol) (PEG) of various molecular weights. By varying their composition, the properties of drug-loaded particles made from these polymers can be optimized. For example, surface properties can be tuned to improve aerosolization efficiency; phagocytic particle clearance in the deep lung can be inhibited by the presence of PEG in the polymer backbone (and ultimately on the particle surface); and continuous drug delivery kinetics can be achieved with control over total duration (hours to weeks). These properties provide a great deal of flexibility for the delivery of a wide range of drugs.

In certain embodiments, biodegradable, biocompatible polymers maybe used to deliver an encapsulated therapeutic agent in addition to the lapachone. Agents that may be encapsulated in the subject compositions include imaging and diagnostic agents (such as radioopaque agents, labeled antibodies, labeled nucleic acid probes, dyes, such as colored or fluorescent dyes, etc.) and adjuvants (radiosensitizers, transfection-enhancing agents (such as chloroquine and analogs thereof), chemotactic agents and chemoattractants, peptides that modulate cell adhesion and/ or cell mobility, cell permeabilizing agents, inhibitors of multidrug resistance and/or efflux pumps, etc.). Particular compounds that have been investigated in combination with lapachones include taxanes (such as paclitaxel and docetaxel), thalidomide, xanthine, and angiogenesis inhibitors. Accordingly, the present invention contemplates compositions that comprise such agents in addition to a lapachone.

The present invention also relates to methods of administering such compositions, e.g., as part of a treatment regimen, for example, by inhalation, by implantation, or by injection, e.g., subcutaneously, intramuscularly, or intravenously.

In certain embodiments, the subject pharmaceutical compositions, under biological conditions, e.g., upon contact with body fluids including blood, spinal fluid, lymph or the like, release the encapsulated drug over a sustained or extended period (as compared to the release from an isotonic saline solution). Such a system may result in prolonged delivery (over, for example, 8 to 800 hours, preferably 24 to 480 or more hours) of effective amounts (e.g., 0.0001 mg/kg/hour to 10 mg/kg/hour) of the drug. This dosage form may be administered as is necessary depending on the subject being treated, the severity of the affliction, the judgment of the prescribing physician, and the like.

In certain embodiments, lapachones selectively target cancer cells or other cells that express or overexpress NAD(P)H:quinone oxidoreductase (NQO1). NQO1 is overexpressed in a number of tumors, including breast, colon, lung, and liver cancers, as compared with surrounding normal tissue (Marin, A., et al., (1997) Br. J. Cancer 76:923–929; Malkinson, A. M., et al., (1992) Cancer Res. 52:4752–4757; Belinsky, M., et al., (1993) Cancer Metastasis Rev. 12:103–117; Joseph, P., et al., (1994) Oncol. Res. 6:525–532). Thus, the invention contemplates the treatment and/or prevention of a cancer characterized by overexpression of NQO1. Furthermore, lapachones act as radiosensitizers in such cells, and thus the invention further contemplates the administration of lapachones in conjunction with radiotherapy, e.g., for the treatment of cancer, whether pre- or post-operative.

2. Definitions

For convenience, before further description of the present invention, certain terms employed in the specification, examples, and appended claims are collected here. These definitions should be read in light of the remainder of the disclosure and understood as by a person of skill in the art.

The term "access device" is an art-recognized term and includes any medical device adapted for gaining or maintaining access to an anatomic area. Such devices are familiar to artisans in the medical and surgical fields. An access device may be a needle, a catheter, a cannula, a trocar, a tubing, a shunt, a drain, or an endoscope such as an otoscope, nasopharyngoscope, bronchoscope, or any other endoscope adapted for use in the head and neck area, or any other medical device suitable for entering or remaining positioned within the preselected anatomic area.

The terms "biocompatible polymer" and "biocompatibility" when used in relation to polymers are art-recognized. For example, biocompatible polymers include polymers that are neither themselves toxic to the host (e.g., an animal or human), nor degrade (if the polymer degrades) at a rate that produces monomeric or oligomeric subunits or other byproducts at toxic concentrations in the host. In certain embodiments of the present invention, biodegradation generally involves degradation of the polymer in an organism, e.g., into its monomeric subunits, which may be known to be effectively non-toxic. Intermediate oligomeric products resulting from such degradation may have different toxicological properties, however, or biodegradation may involve oxidation or other biochemical reactions that generate molecules other than monomeric subunits of the polymer. Consequently, in certain embodiments, toxicology of a biodegradable polymer intended for in vivo use, such as implantation or injection into a patient, may be determined after one or more toxicity analyses. It is not necessary that any subject composition have a purity of 100% to be deemed biocompatible. Hence, a subject composition may comprise 99%, 98%, 97%, 96%, 95%, 90% 85%, 80%, 75% or even less of biocompatible polymers, e.g., including polymers and other materials and excipients described herein, and still be biocompatible.

To determine whether a polymer or other material is biocompatible, it may be necessary to conduct a toxicity analysis. Such assays are well known in the art. One example of such an assay may be performed with live carcinoma cells, such as GT3TKB tumor cells, in the following manner: the sample is degraded in 1 M NaOH at 37° C. until complete degradation is observed. The solution is then neutralized with 1 M HCl. About 200 μL of various concentrations of the degraded sample products are placed in 96-well tissue culture plates and seeded with human gastric carcinoma cells (GT3TKB) at 104/well density. The degraded sample products are incubated with the GT3TKB cells for 48 hours. The results of the assay may be plotted as % relative growth vs. concentration of degraded sample in the tissue-culture well. In addition, polymers and formulations of the present invention may also be evaluated by well-known in vivo tests, such as subcutaneous implantations in rats to confirm that they do not cause significant levels of irritation or inflammation at the subcutaneous implantation sites.

The term "biodegradable" is art-recognized, and includes polymers, compositions and formulations, such as those described herein, that are intended to degrade during use. Biodegradable polymers typically differ from non-biodegradable polymers in that the former may be degraded during use. In certain embodiments, such use involves in vivo use, such as in vivo therapy, and in other certain embodiments, such use involves in vitro use. In general, degradation attributable to biodegradability involves the degradation of a biodegradable polymer into its component subunits, or digestion, e.g., by a biochemical process, of the polymer into smaller, non-polymeric subunits. In certain embodiments, two different types of biodegradation may generally be identified. For example, one type of biodegradation may involve cleavage of bonds (whether covalent or otherwise) in the polymer backbone. In such biodegradation, monomers and oligomers typically result, and even more typically, such biodegradation occurs by cleavage of a bond connecting one or more of subunits of a polymer. In contrast, another type of biodegradation may involve cleavage of a bond (whether covalent or otherwise) internal to sidechain or that connects a side chain to the polymer backbone. For example, a therapeutic agent or other chemical moiety attached as a side chain to the polymer backbone may be released by biodegradation. In certain embodiments, one or the other or both generally types of biodegradation may occur during use of a polymer.

As used herein, the term "biodegradation" encompasses both general types of biodegradation. The degradation rate of a biodegradable polymer often depends in part on a variety of factors, including the chemical identity of the linkage responsible for any degradation, the molecular weight, crystallinity, biostability, and degree of cross-linking of such polymer, the physical characteristics (e.g., shape and size) of the implant, and the mode and location of administration. For example, the greater the molecular weight, the higher the degree of crystallinity, and/or the greater the biostability, the biodegradation of any biodegradable polymer is usually slower. The term "biodegradable" is intended to cover materials and processes also termed "bioerodible".

In certain embodiments wherein the biodegradable polymer also has a therapeutic agent or other material associated with it, the biodegradation rate of such polymer may be characterized by a release rate of such materials. In such circumstances, the biodegradation rate may depend on not only the chemical identity and physical characteristics of the polymer, but also on the identity of material(s) incorporated therein.

In certain embodiments, polymeric formulations of the present invention biodegrade within a period that is acceptable in the desired application. In certain embodiments, such as in vivo therapy, such degradation occurs in a period usually less than about five years, one year, six months, three months, one month, fifteen days, five days, three days, or even one day on exposure to a physiological solution with a pH between 6 and 8 having a temperature of between 25 and 37° C. In other embodiments, the polymer degrades in a period of between about one hour and several weeks, depending on the desired application.

The term "drug delivery device" is an art-recognized term and refers to any medical device suitable for the application of a drug or therapeutic agent to a targeted organ or anatomic region. The term includes, without limitation, those formulations of the compositions of the present invention that release the therapeutic agent into the surrounding tissues of an anatomic area. The term further includes those devices that transport or accomplish the instillation of the compositions of the present invention towards the targeted organ or anatomic area, even if the device itself is not formulated to include the composition. As an example, a needle or a catheter through which the composition is inserted into an anatomic area or into a blood vessel or other structure related to the anatomic area is understood to be a drug delivery device. As a further example, a stent or a shunt or a catheter that has the composition included in its substance or coated on its surface is understood to be a drug delivery device.

When used with respect to a therapeutic agent or other material, the term "sustained release" is art-recognized. For example, a subject composition which releases a substance over time may exhibit sustained release characteristics, in contrast to a bolus type administration in which the entire amount of the substance is made biologically available at one time. For example, in particular embodiments, upon contact with body fluids including blood, spinal fluid, lymph or the like, the polymer matrices (formulated as provided herein and otherwise as known to one of skill in the art) may undergo gradual degradation (e.g., through hydrolysis) with concomitant release of any material incorporated therein, e.g., an therapeutic and/or biologically active agent, for a sustained or extended period (as compared to the release from a bolus). This release may result in prolonged delivery of therapeutically effective amounts of any incorporated therapeutic agent. Sustained release will vary in certain embodiments as described in greater detail below.

The term "delivery agent" is an art-recognized term, and includes molecules that facilitate the intracellular delivery of a therapeutic agent or other material. Examples of delivery agents include: sterols (e.g., cholesterol) and lipids (e.g., a cationic lipid, virosome or liposome).

The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity of the host animal.

The term "microspheres" is art-recognized, and includes substantially spherical colloidal structures, e.g., formed from biocompatible polymers such as subject compositions, having a size ranging from about one or greater up to about 1000 microns. In general, "microcapsules", also an art-recognized term, may be distinguished from microspheres, because microcapsules are generally covered by a substance of some type, such as a polymeric formulation. The term "microparticles" is art-recognized, and includes microspheres and microcapsules, as well as structures that may not be readily placed into either of the above two categories, all with dimensions on average of less than about 1000 microns. If the structures are less than about one micron in diameter, then the corresponding art-recognized terms "nanosphere," "nanocapsule," and "nanoparticle" may be utilized. In certain embodiments, the nanospheres, nancapsules and nanoparticles have a size an average diameter of about 500, 200, 100, 50 or 10 nm.

A composition comprising microspheres may include particles of a range of particle sizes. In certain embodiments, the particle size distribution may be uniform, e.g., within less than about a 20% standard deviation of the median volume diameter, and in other embodiments, still more uniform or within about 10% of the median volume diameter.

The phrases "parenteral administration" and "administered parenterally" are art-recognized terms, and include modes of administration other than enteral and topical administration, such as injections, and include without limitation intravenous, intramuscular, intrapleural, intravascular, intrapericardial, intraarterial, intrathecal, intracapsular, intraorbital, intracardiac, intradennal, intraperitoneal, transtracheal, subcutaneous, subcuticular, intra-articular, subcapsular, subarachnoid, intraspinal and intrasternal injection and infusion.

The term "treating" is art-recognized and includes preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic, (i.e., it is intended to diminish, ameliorate, or stabilize the existing unwanted condition or side effects thereof).

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salts" is art-recognized, and includes relatively non-toxic, inorganic and organic acid addition salts of compositions, including without limitation, analgesic agents, therapeutic agents, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, *J. Pharm. Sci.* 66: 1–19 (1977).

A "patient," "subject," or "host" to be treated by the subject method may mean either a human or non-human animal, such as primates, mammals, and vertebrates.

The phrases "systemic administration," "administered systemically," "peripheral administration" and "administered peripherally" are art-recognized, and include the administration of a subject composition, therapeutic or other material at a site remote from the disease being treated. Administration of an agent directly into, onto, or in the vicinity of a lesion of the disease being treated, even if the agent is subsequently distributed systemically, may be termed "local" or "topical" or "regional" administration, other than directly into the central nervous system, e.g., by subcutaneous administration, such that it enters the patient's system and, thus, is subject to metabolism and other like processes.

The phrase "therapeutically effective amount" is an art-recognized term. In certain embodiments, the term refers to an amount of the therapeutic agent that, when incorporated into a polymer of the present invention, produces some desired effect at a reasonable benefit/risk ratio applicable to any medical treatment. In certain embodiments, the term refers to that amount necessary or sufficient to eliminate or reduce sensations of pain for a period of time. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation.

The term "$ED_{50}$" is art-recognized. In certain embodiments, $ED_{50}$ means the dose of a drug that produces 50% of its maximum response or effect, or, alternatively, the dose that produces a pre-determined response in 50% of test subjects or preparations.

The term "$LD_{50}$" is art-recognized. In certain embodiments, $LD_{50}$ means the dose of a drug that is lethal in 50% of test subjects. The term "therapeutic index" is an art-recognized term that refers to the therapeutic index of a drug, defined as $LD_{50}/ED_{50}$.

The terms "incorporated" and "encapsulated" are art-recognized when used in reference to a therapeutic agent, or other material and a polymeric composition, such as a composition of the present invention. In certain embodiments, these terms include incorporating, formulating, or otherwise including such agent into a composition that allows for release, such as sustained release, of such agent in the desired application. The terms contemplate any manner by which a therapeutic agent or other material is incorporated into a polymer matrix, including for example: attached to a monomer of such polymer (by covalent, ionic, or other binding interaction), physical admixture, enveloping the agent in a coating layer of polymer, and having such monomer be part of the polymerization to give a polymeric formulation, distributed throughout the polymeric matrix, appended to the surface of the polymeric matrix (by covalent or other binding interactions), encapsulated inside the polymeric matrix, etc. The term "co-incorporation" or "co-encapsulation" refers to-the incorporation of a therapeutic agent or other material and at least one other therapeutic agent or other material in a subject composition.

More specifically, the physical form in which any therapeutic agent or other material is encapsulated in polymers may vary with the particular embodiment. For example, a therapeutic agent or other material may be first encapsulated in a microsphere and then combined with the polymer in such a way that at least a portion of the microsphere structure is maintained. Alternatively, a therapeutic agent or other material may be sufficiently immiscible in the polymer of the invention that it is dispersed as small droplets, rather than being dissolved, in the polymer. Any form of encapsulation or incorporation is contemplated by the present invention, in so much as the release, preferably sustained release, of any encapsulated therapeutic agent or other material determines whether the form of encapsulation is sufficiently acceptable for any particular use.

The term "biocompatible plasticizer" is art-recognized, and includes materials which are soluble or dispersible in the compositions of the present invention, which increase the flexibility of the polymer matrix, and which, in the amounts employed, are biocompatible. Suitable plasticizers are well known in the art and include those disclosed in U.S. Pat. Nos. 2,784,127 and 4,444,933. Specific plasticizers include, by way of example, acetyl tri-n-butyl citrate (c. 20 weight percent or less), acetyltrihexyl citrate (c. 20 weight percent or less), butyl benzyl phthalate, dibutylphthalate, dioctylphthalate, n-butyryl tri-n-hexyl citrate, diethylene glycol dibenzoate (c. 20 weight percent or less) and the like.

The terms 'amine' and 'amino' are art-recognized and refer to both unsubstituted and substituted amines as well as ammonium salts, e.g., as can be represented by the general formula:

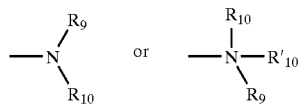

wherein $R_9$, $R_{10}$, and $R'_{10}$ each independently represent hydrogen or a hydrocarbon substituent, or $R_9$ and $R_{10}$ taken together with the N atom to which they are attached complete a heterocycle having from 4 to 8 atoms in the ring structure. In preferred embodiments, none of $R_9$, $R_{10}$, and $R'_{10}$ is acyl, e.g., $R_9$, $R_{10}$, and $R'_{10}$ are selected from hydrogen, alkyl, heteroalkyl, aryl, heteroaryl, carbocyclic aliphatic, and heterocyclic aliphatic. The term 'alkylamine' as used herein means an amine group, as defined above, having at least one substituted or unsubstituted alkyl attached thereto. Amino groups that are positively charged (e.g., $R'_{10}$ is present) are referred to as 'ammonium' groups. In amino groups other than ammonium groups, the amine is preferably basic, e.g., its conjugate acid has a $pK_a$ above 7.

The terms 'amido' and 'amide' are art-recognized as an amino-substituted carbonyl, such as a moiety that can be represented by the general formula:

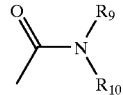

wherein $R_9$ and $R_{10}$ are as defined above. In certain embodiments, the amide will include imides.

'Alkyl' refers to a saturated or unsaturated hydrocarbon chain having 1 to 18 carbon atoms, preferably 1 to 12, more preferably 1 to 6, more preferably still 1 to 4 carbon atoms. Alkyl chains may be straight (e.g., n-butyl) or branched (e.g., sec-butyl, isobutyl, or t-butyl). Preferred branched alkyls have one or two branches, preferably one branch. Preferred alkyls are saturated. Unsaturated alkyls have one or more double bonds and/or one or more triple bonds. Preferred unsaturated alkyls have one or two double bonds or one triple bond, more preferably one double bond. Alkyl chains may be unsubstituted or substituted with from 1 to 4 substituents. Preferred alkyls are unsubstituted. Preferred substituted alkyls are mono-, di-, or trisubstituted. Preferred alkyl substituents include halo, haloalkyl, hydroxy, aryl (e.g., phenyl, tolyl, alkoxyphenyl, alkyloxycarbonylphenyl, halophenyl), heterocyclyl, and heteroaryl.

The terms 'alkenyl' and 'alkynyl' refer to unsaturated aliphatic groups analogous in length and possible substitution to the alkyls described above, but that contain at least one double or triple bond, respectively. When not otherwise indicated, the terms alkenyl and alkynyl preferably refer to lower alkenyl and lower alkynyl groups, respectively. When the term alkyl is present in a list with the terms alkenyl and alkynyl, the term alkyl refers to saturated alkyls exclusive of alkenyls and alkynyls.

The terms 'alkoxyl' and 'alkoxy' as used herein refer to an —O-alkyl group. Representative alkoxyl groups include methoxy, ethoxy, propyloxy, tert-butoxy, and the like. An 'ether' is two hydrocarbons covalently linked by an oxygen. Accordingly, the substituent of a hydrocarbon that renders that hydrocarbon an ether can be an alkoxyl, or another moiety such as —O-aryl, —O-heteroaryl, —O-heteroalkyl, —O-aralkyl, —O-heteroaralkyl, —O-carbocyclic aliphatic, or —O-heterocyclic aliphatic.

The term 'alkylthio' refers to an —S-alkyl group. Representative alkylthio groups include methylthio, ethylthio, and the like. 'Thioether' refers to a sulfur atom bound to two hydrocarbon substituents, e.g., an ether wherein the oxygen is replaced by sulfur. Thus, a thioether substituent on a carbon atom refers to a hydrocarbon-substituted sulfur atom substituent, such as alkylthio or arylthio, etc.

The term 'aralkyl', as used herein, refers to an alkyl group substituted with an aryl group.

'Aryl ring' refers to an aromatic hydrocarbon ring system. Aromatic rings are monocyclic or fused bicyclic ring systems, such as phenyl, naphthyl, etc. Monocyclic aromatic rings contain from about 5 to about 10 carbon atoms, preferably from 5 to 7 carbon atoms, and most preferably from 5 to 6 carbon atoms in the ring. Bicyclic aromatic rings contain from 8 to 12 carbon atoms, preferably 9 or 10 carbon atoms in the ring. The term 'aryl' also includes bicyclic ring systems wherein only one of the rings is aromatic, e.g., the other ring is cycloalkyl, cycloalkenyl, or heterocyclyl. Aromatic rings may be unsubstituted or substituted with from 1 to about 5 substituents on the ring. Preferred aromatic ring substituents include: halo, cyano, lower alkyl, heteroalkyl, haloalkyl, phenyl, phenoxy, or any combination thereof. More preferred substituents include lower alkyl, cyano, halo, and haloalkyl.

'Carbocyclic aliphatic ring' refers to a saturated or unsaturated hydrocarbon ring. Carbocyclic aliphatic rings are not aromatic. Carbocyclic aliphatic rings are monocyclic, or are fused, spiro, or bridged bicyclic ring systems. Monocyclic carbocyclic aliphatic rings contain from about 4 to about 10 carbon atoms, preferably from 4 to 7 carbon atoms, and most preferably from 5 to 6 carbon atoms in the ring. Bicyclic carbocyclic aliphatic rings contain from 8 to 12 carbon atoms, preferably from 9 to 10 carbon atoms in the ring. Carbocyclic aliphatic rings may be unsubstituted or substituted with from 1 to 4 substituents on the ring. Preferred carbocyclic aliphatic ring substituents include halo, cyano, alkyl, heteroalkyl, haloalkyl, phenyl, phenoxy or any combination thereof. More preferred substituents include halo and haloalkyl. Preferred carbocyclic aliphatic rings include cyclopentyl, cyclohexyl, cyclohexenyl, cycloheptyl, and cyclooctyl. More preferred carbocyclic aliphatic rings include cyclohexyl, cycloheptyl, and cyclooctyl.

The term 'carbonyl' is art-recognized and includes such moieties as can be represented by the general formula:

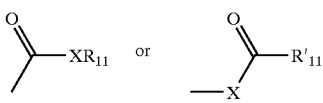

wherein X is a bond or represents an oxygen or a sulfur, and $R_{11}$ represents a hydrogen, hydrocarbon substituent, or a pharmaceutically acceptable salt, $R_{11'}$ represents a hydrogen or hydrocarbon substituent. Where X is an oxygen and $R_{11}$ or $R_{11'}$ is not hydrogen, the formula represents an 'ester'. Where X is an oxygen, and $R_{11}$ is as defined above, the moiety is referred to herein as a carboxyl group, and particularly when $R_{11}$ is a hydrogen, the formula represents a 'carboxylic acid'. Where X is an oxygen, and $R_{11'}$ is hydrogen, the formula represents a 'formate'. In general, where the oxygen atom of the above formula is replaced by sulfur, the formula represents a 'thiocarbonyl' group. Where X is a sulfur and $R_{11}$ or $R_{11'}$ is not hydrogen, the formula represents a 'thioester.' Where X is a sulfur and $R_{11}$ is hydrogen, the formula represents a 'thiocarboxylic acid.' Where X is a sulfur and $R_{11'}$ is hydrogen, the formula represents a 'thioformate.' On the other hand, where X is a bond, $R_{11}$ is not hydrogen, and the carbonyl is bound to a hydrocarbon, the above formula represents a 'ketone' group. Where X is a bond, $R_{11}$ is hydrogen, and the carbonyl is bound to a hydrocarbon, the above formula represents an 'aldehyde' or 'formyl' group.

'Ci alkyl' is an alkyl chain having i member atoms. For example, C4 alkyls contain four carbon member atoms. C4 alkyls containing may be saturated or unsaturated with one or two double bonds (cis or trans) or one triple bond. Preferred C4 alkyls are saturated. Preferred unsaturated C4 alkyl have one double bond. C4 alkyl may be unsubstituted or substituted with one or two substituents. Preferred substituents include lower alkyl, lower heteroalkyl, cyano, halo, and haloalkyl.

'Halogen' refers to fluoro, chloro, bromo, or iodo substituents. Preferred halo are fluoro, chloro and bromo; more preferred are chloro and fluoro.

'Haloalkyl' refers to a straight, branched, or cyclic hydrocarbon substituted with one or more halo substituents. Preferred haloalkyl are C1–C12; more preferred are C1–C6; more preferred still are C1–C3. Preferred halo substituents are fluoro and chloro. The most preferred haloalkyl is trifluoromethyl.

'Heteroalkyl' is a saturated or unsaturated chain of carbon atoms and at least one heteroatom, wherein no two heteroatoms are adjacent. Heteroalkyl chains contain from 1 to 18 member atoms (carbon and heteroatoms) in the chain, preferably 1 to 12, more preferably 1 to 6, more preferably still 1 to 4. Heteroalkyl chains may be straight or branched. Preferred branched heteroalkyl have one or two branches, preferably one branch. Preferred heteroalkyl are saturated. Unsaturated heteroalkyl have one or more double bonds and/or one or more triple bonds. Preferred unsaturated heteroalkyl have one or two double bonds or one triple bond, more preferably one double bond. Heteroalkyl chains may be unsubstituted or substituted with from 1 to about 4 substituents unless otherwise specified. Preferred heteroalkyl are unsubstituted. Preferred heteroalkyl substituents include halo, aryl (e.g., phenyl, tolyl, alkoxyphenyl, alkoxycarbonylphenyl, halophenyl), heterocyclyl, heteroaryl. For example, alkyl chains substituted with the following substituents are heteroalkyl: alkoxy (e.g., methoxy, ethoxy, propoxy, butoxy, pentoxy), aryloxy (e.g., phenoxy, chlorophenoxy, tolyloxy, methoxyphenoxy, benzyloxy, alkoxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkoxycarbonylphenylthio), amino (e.g., amino, mono- and di- C1–C3 alkylamino, methylphenylamino, methylbenzylamino, C1–C3 alkylamido, carbamamido, ureido, guanidino).

'Heteroatom' refers to a multivalent non-carbon atom, such as a boron, phosphorous, silicon, nitrogen, sulfur, or oxygen atom, preferably a nitrogen, sulfur, or oxygen atom. Groups containing more than one heteroatom may contain different heteroatoms.

'Heteroaryl ring' refers to an aromatic ring system containing carbon and from 1 to about 4 heteroatoms in the ring. Heteroaromatic rings are monocyclic or fused bicyclic ring systems. Monocyclic heteroaromatic rings contain from about 5 to about 10 member atoms (carbon and heteroatoms), preferably from 5 to 7, and most preferably from 5 to 6 in the ring. Bicyclic heteroaromatic rings contain from 8 to 12 member atoms, preferably 9 or 10 member atoms in the ring. The term 'heteroaryl' also includes bicyclic ring systems wherein only one of the rings is aromatic, e.g., the other ring is cycloalkyl, cycloalkenyl, or heterocyclyl. Heteroaromatic rings may be unsubstituted or substituted with from 1 to about 4 substituents on the ring. Preferred heteroaromatic ring substituents include halo, cyano, lower alkyl, heteroalkyl, haloalkyl, phenyl, phenoxy or any combination thereof. Preferred heteroaromatic rings include thienyl, thiazolyl, oxazolyl, pyrrolyl, purinyl, pyrimidyl, pyridyl, and furanyl. More preferred heteroaromatic rings include thienyl, furanyl, and pyridyl.

'Heterocyclic aliphatic ring' is a non-aromatic saturated or unsaturated ring containing carbon and from 1 to about 4 heteroatoms in the ring, wherein no two heteroatoms are adjacent in the ring and preferably no carbon in the ring attached to a heteroatom also has a hydroxyl, amino, or thiol group attached to it. Heterocyclic aliphatic rings are monocyclic, or are fused or bridged bicyclic ring systems. Monocyclic heterocyclic aliphatic rings contain from about 4 to about 10 member atoms (carbon and heteroatoms), preferably from 4 to 7, and most preferably from 5 to 6 member atoms in the ring. Bicyclic heterocyclic aliphatic rings contain from 8 to 12 member atoms, preferably 9 or 10 member atoms in the ring. Heterocyclic aliphatic rings may be unsubstituted or substituted with from 1 to about 4 substituents on the ring. Preferred heterocyclic aliphatic ring substituents include halo, cyano, lower alkyl, heteroalkyl, haloalkyl, phenyl, phenoxy or any combination thereof. More preferred substituents include halo and haloalkyl. Heterocyclyl groups include, for example, thiophene, thianthrene, furan, pyran, isobenzofuran, chromene, xanthene, phenoxathin, pyrrole, imidazole, pyrazole, isothiazole, isoxazole, pyridine, pyrazine, pyrimidine, pyridazine, indolizine, isoindole, indole, indazole, purine, quinolizine, isoquinoline, hydantoin, oxazoline, imidazolinetrione, triazolinone, quinoline, phthalazine, naphthyridine, quinoxaline, quinazoline, quinoline, pteridine, carbazole, carboline, phenanthridine, acridine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. Preferred heterocyclic aliphatic rings include piperazyl, morpholinyl, tetrahydrofuranyl, tetrahydropyranyl and piperidyl. Heterocycles can also be polycycles.

The term 'hydroxyl' means —OH.

'Lower alkyl' refers to an alkyl chain comprised of 1 to 4, preferably 1 to 3 carbon member atoms, more preferably 1 or 2 carbon member atoms. Lower alkyls may be saturated or unsaturated. Preferred lower alkyls are saturated. Lower alkyls may be unsubstituted or substituted with one or about two substituents. Preferred substituents on lower alkyl include cyano, halo, trifluoromethyl, amino, and hydroxyl. Throughout the application, preferred alkyl groups are lower alkyls. In preferred embodiments, a substituent designated herein as alkyl is a lower alkyl. Likewise, 'lower alkenyl' and 'lower alkynyl' have similar chain lengths.

'Lower heteroalkyl' refers to a heteroalkyl chain comprised of 1 to 4, preferably 1 to 3 member atoms, more preferably 1 to 2 member atoms. Lower heteroalkyl contain one or two non-adjacent heteroatom member atoms. Preferred lower heteroalkyl contain one heteroatom member atom. Lower heteroalkyl may be saturated or unsaturated. Preferred lower heteroalkyl are saturated. Lower heteroalkyl may be unsubstituted or substituted with one or about two substituents. Preferred substituents on lower heteroalkyl include cyano, halo, trifluoromethyl, and hydroxyl.

'Mi heteroalkyl' is a heteroalkyl chain having i member atoms. For example, M4 heteroalkyls contain one or two non-adjacent heteroatom member atoms. M4 heteroalkyls containing 1 heteroatom member atom may be saturated or unsaturated with one double bond (cis or trans) or one triple bond. Preferred M4 heteroalkyl containing 2 heteroatom member atoms are saturated. Preferred unsaturated M4 heteroalkyl have one double bond. M4 heteroalkyl may be unsubstituted or substituted with one or two substituents. Preferred substituents include lower alkyl, lower heteroalkyl, cyano, halo, and haloalkyl.

'Member atom' refers to a polyvalent atom (e.g., C, O, N, or S atom) in a chain or ring system that constitutes a part of the chain or ring. For example, in cresol, six carbon atoms are member atoms of the ring and the oxygen atom and the carbon atom of the methyl substituent are not member atoms of the ring.

'Pharmaceutically acceptable salt' refers to a cationic salt formed at any acidic (e.g., hydroxamic or carboxylic acid) group, or an anionic salt formed at any basic (e.g., amino or guanidino) group. Such salts are well known in the art. See e.g., PCT Publication 87/05297, Johnston et al., published Sep. 11, 1987, incorporated herein by reference. Such salts are made by methods known to one of ordinary skill in the art. It is recognized that the skilled artisan may prefer one salt over another for improved solubility, stability, formulation ease, price and the like. Determination and optimization of such salts is within the purview of the skilled artisan's practice. Preferred cations include the alkali metals (such as sodium and potassium), and alkaline earth metals (such as magnesium and calcium) and organic cations, such as trimethylammonium, tetrabutylammonium, etc. Preferred anions include halides (such as chloride), sulfonates, carboxylates, phosphates, and the like. Clearly contemplated in such salts are addition salts that may provide an optical center where once there was none. For example, a chiral tartrate salt may be prepared from the compounds of the invention. This definition includes such chiral salts.

'Phenyl' is a six-membered monocyclic aromatic ring that may or may not be substituted with from 1 to 5 substituents. The substituents may be located at the ortho, meta or para position on the phenyl ring, or any combination thereof. Preferred phenyl substituents include: halo, cyano, lower alkyl, heteroalkyl, haloalkyl, phenyl, phenoxy or any combination thereof. More preferred substituents on the phenyl ring include halo and haloalkyl. The most preferred substituent is halo.

The term 'sulfhydryl' means —SH, and the term 'sulfonyl' means —SO$_2$—.

A 'substitution' or 'substituent' on a small organic molecule generally refers to a position on a multi-valent atom bound to a moiety other than hydrogen, e.g., a position on a chain or ring exclusive of the member atoms of the chain or ring. Such moieties include those defined herein and others as are known in the art, for example, halogen, alkyl, alkenyl, alkynyl, azide, haloalkyl, hydroxyl, carbonyl (such as carboxyl, alkoxycarbonyl, formyl, ketone, or acyl), thiocarbonyl (such as thioester, thioacetate, or thioformate), alkoxyl, phosphoryl, phosphonate, phosphinate, amine, amide, amidine, imine, cyano, nitro, azido, sulfhydryl, alkylthio, sulfate, sulfonate, sulfamoyl, sulfonamido, sulfonyl, silyl, ether, cycloalkyl, heterocyclyl, heteroalkyl, heteroalkenyl, and heteroalkynyl, heteroaralkyl, aralkyl, aryl or heteroaryl. It will be understood by those skilled in the art that certain substituents, such as aryl, heteroaryl, polycyclyl, alkoxy, alkylamino, alkyl, cycloalkyl, heterocyclyl, alkenyl, alkynyl, heteroalkyl, heteroalkenyl, and heteroalkynyl, can themselves be substituted, if appropriate. This invention is not intended to be limited in any manner by the permissible substituents of organic compounds. It will be understood that 'substitution' or 'substituted with' includes the implicit proviso that such substitution is in accordance with permitted valence of the substituted atom and the substituent, and that the substitution results in a stable compound, e.g., which does not spontaneously undergo transformation such as by rearrangement, cyclization, elimination, hydrolysis, etc.

As used herein, the definition of each expression, e.g., alkyl, m, n, etc., when it occurs more than once in any structure, is intended to be independent of its definition elsewhere in the same structure.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl, and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The phrase 'protecting group' as used herein means temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991; and Kocienski, P. J. *Protecting Groups*, Georg Thieme Verlag: New York, 1994).

For purposes of this invention, the chemical elements are identified in accordance with the Periodic Table of the Elements, CAS version, Handbook of Chemistry and Physics, 67th Ed., 1986–87, inside cover. Also for purposes of this invention, the term 'hydrocarbon' is contemplated to include all permissible compounds or moieties having at least one carbon-hydrogen bond. In a broad aspect, the permissible hydrocarbons include acyclic and cyclic, branched and unbranched, carbocyclic and heterocyclic, aromatic and nonaromatic organic compounds which can be substituted or unsubstituted.

Contemplated equivalents of the compounds described herein include compounds which otherwise correspond thereto, and which have the same useful properties thereof, wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

3. Lapachones and Methods of Preparing them

The present invention contemplates the delivery of β-lapachone and/or derivatives or analogs thereof, collectively referred to herein as lapachones. A wide variety of lapachone analogs which retain a pharmacologically important quinone moiety have been described. See, for example, U.S. Pat. Nos. 6,245,807, 5,763,625, 5,824,700, 5,969,163, and 5,977,187, PCT publications WO 94/04145 and WO 00/61142, as well as Sabba. et al., *J Med Chem* 27:990–994 (1984); Molina Portela and Stoppani, *Biochem Pharm* 51:275–283 (1996); and Goncalves et al., *Molecular and Biochemical Parasitology* 1:167–176 (1998). Strategies for preparing various lapachones are described in U.S. Pat. Nos. 6,458,974, 5,969,163, and 5,763,625.

In certain embodiments, a lapachone has a structure of either Formula I or Formula II:

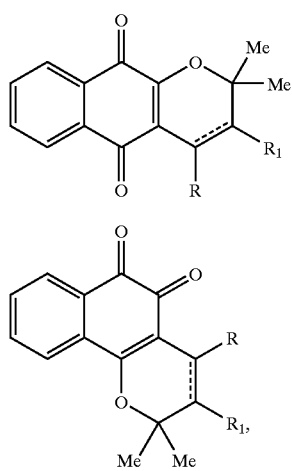

Formula I

Formula II wherein R and $R_1$ each independently represent H, hydroxy, amino, amido, sulfhydryl, halogen, or substituted or unsubstituted alkyl, alkenyl, heteroalkyl, carbocyclic aliphatic, carbocyclic aliphatic alkyl, aryl, aralkyl, heterocyclic aliphatic, heterocyclic aliphatic alkyl, heteroaryl, heteroaralkyl, or alkoxy, or a pharmaceutically acceptable salt thereof.

Alkyl groups preferably have from 1 to about 15 carbon atoms, more preferably from 1 to about 10 carbon atoms, still more preferably from 1 to about 6 carbon atoms. Alkenyl groups preferably have from 2 to 15 carbon atoms, more preferably from 2 to about 10 carbon atoms, still more preferably from 2 to about 6 carbon atoms. Especially preferred alkenyl groups have 3 carbon atoms (i.e., 1-propenyl or 2-propenyl), with the allyl moiety being particularly preferred. Phenyl and naphthyl are generally preferred aryl groups. Alkoxy groups include those alkoxy groups having one or more oxygen linkage and preferably have from 1 to 15 carbon atoms, more preferably from 1 to about 6 carbon atoms. Substituted R and $R_1$ groups may be substituted at one or more available positions by one or more suitable groups such as, for example, alkyl groups such as alkyl groups having from 1 to 10 carbon atoms or from 1 to 6 carbon atoms, alkenyl groups such as alkenyl groups having from 2 to 10 carbon atoms or 2 to 6 carbon atoms, aryl groups having from 6 to 10 carbon atoms, halogen such as fluoro, chloro, and bromo, and N, O, or S, including heteroalkyl, e.g., heteroalkyl having one or more of said hetero atom linkages (and thus including alkoxy, aminoalkyl and thioalkyl) and from 1 to 10 carbon atoms or from 1 to 6 carbon atoms.

In certain embodiments, the lapachone is provided as an inclusion complex with a cyclodextrin, preferably a β-cyclodextrin, such as hydroxypropyl β-cyclodextrin, e.g., to improve the solubility of the lapachone. Such complexes may be administered in admixture with a polymer, or in non-polymeric formulations, such as injectable solutions and oral formulations.

In certain embodiments, the lapachone is provided as a prodrug. Although many strategies for preparing prodrugs are widely known in the art, one particular method of forming prodrugs of lapachone involves the formation of a Schiff base by condensing the lapachone with a primary amine, such as a substituted or unsubstituted alkyl, carbocyclic aliphatic, carbocyclic aliphatic alkyl, aryl, aralkyl, heterocyclic aliphatic, heterocyclic aliphatic alkyl, heteroaryl, or heteroaralkyl amine. The resulting prodrug may thus have a structure of Formula III:

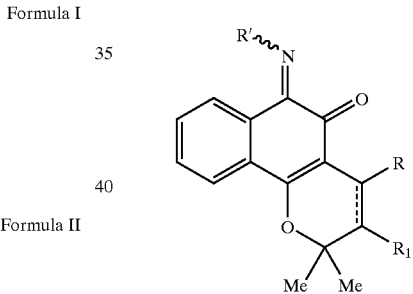

wherein R and $R_1$ are as defined above, and R' represents a substituted or unsubstituted alkyl, carbocyclic aliphatic, carbocyclic aliphatic alkyl, aryl, aralkyl, heterocyclic aliphatic, heterocyclic aliphatic alkyl, heteroaryl, or heteroaralkyl substituent. In certain embodiments, R' is an alkyl or aryl group. In embodiments wherein R' represents phenyl, the phenyl ring is optionally substituted, e.g., with a nitro, methyl, methoxy, or halogen substituent. Varying the substituent of the phenyl ring may affect the rate of hydrolysis of the Schiff base, and thereby affect the rate at which the prodrug is rendered active in a physiological environment.

4. Polymer Vehicles

A variety of polymers can be used in the preparation of lapachone formulations. In certain embodiments, the polymer is biocompatible and biodegradable, while in other embodiments, the polymer is merely biocompatible. Suitable polymers include polypropylene, polyester, polyethylene vinyl acetate (PVA or EVA), polysebacic acid (PSA) polyethylene oxide (PEO; =poly(ethylene glycol), PEG), polypropylene oxide, polycarboxylic acids, polyalkylacrylates, cellulose ethers, silicone, poly(dl-lactide-co-glycolide) (PLGA), various Eudragits (for example, NE30D, RS PO and RL PO), polyalkyl-alkyacrylate copolymers, polyester-polyurethane block copolymers, polyether-polyurethane block copolymers, polydioxanone, poly-(β-hydroxybutyrate), polylactic acid (PLA), polycaprolactone, polyglycolic acid (PGA), and copolymers thereof, including PEG-PLA, PEG-PSA, or PEG-PLGA copolymers. Certain such copolymers are discussed in detail in PCT publication WO 03/00237.

In certain preferred embodiments wherein the polymer is a copolymer of PEO and another polymer, such as PSA, PLA, or PLGA, the ratio of PEG to its comonomer is between 5:50 and 5:120, preferably between about 5:70 and about 5:100.

In certain embodiments, the polymeric chains of the subject compositions have molecular weights ($M_w$) ranging from about 2000 or less to about 300,000, 600,000 or 1,000,000 or more daltons, or alternatively at least about 10,000, 20,000, 30,000, 40,000, or 50,000 daltons, more particularly at least about 100,000 daltons. Number-average molecular weight ($M_n$) may also vary widely, but generally fall in the range of about 1,000 to about 200,000 daltons, preferably from about 10,000 to about 100,000 daltons and, even more preferably, from about 8,000 to about 50,000 daltons. Most preferably, $M_n$ varies between about 12,000 and 45,000 daltons. Within a given sample of a subject polymer, a wide range of molecular weights may be present. For example, molecules within the sample may have molecular weights that differ by a factor of 2, 5, 10, 20, 50, 100, or more, or that differ from the average molecular weight by a factor of 2, 5, 10, 20, 50, 100, or more.

One method to determine molecular weight is by gel permeation chromatography ("GPC"), e.g., mixed bed columns, $CH_2Cl_2$ solvent, light scattering detector, and off-line dn/dc. Other methods are known in the art.

In other embodiments, the polymer composition of the invention may be a flexible or flowable material. When the polymer used is itself flowable, the polymer composition of the invention, even when viscous, need not include a biocompatible solvent to be flowable, although trace or residual amounts of biocompatible solvents may still be present.

While it is possible that the biodegradable polymer or the lapachone or other biologically active agent may be dissolved in a small quantity of a solvent that is non-toxic to more efficiently produce an amorphous, monolithic distribution or a fine dispersion of the biologically active agent in the flexible or flowable composition, it is an advantage of the invention that, in a preferred embodiment, no solvent is needed to form a flowable composition. Moreover, the use of solvents is preferably avoided, because once a polymer composition containing solvent is placed totally or partially within the body, the solvent dissipates or diffuses away from the polymer and must be processed and eliminated by the body, placing an extra burden on the body's clearance ability at a time when the illness (and/or other treatments for the illness) may have already deleteriously affected it.

However, when a solvent is used to facilitate mixing or to maintain the flowability of the polymer composition of the invention, it should be non-toxic, otherwise biocompatible, and should be used in relatively small amounts. Solvents that are toxic should not be used in any material to be placed even partially within a living body. Such a solvent also must not cause substantial tissue irritation or necrosis at the site of administration.

Examples of suitable biocompatible solvents, when used, include N-methyl-2-pyrrolidone, 2-pyrrolidone, ethanol, propylene glycol, acetone, methyl acetate, ethyl acetate, methyl ethyl ketone, dimethylformamide, dimethyl sulfoxide, tetrahydrofuran, caprolactam, oleic acid, or 1-dodecylazacycoheptanone. Preferred solvents include N-methyl pyrrolidone, 2-pyrrolidone, dimethyl sulfoxide, and acetone because of their solvating ability and their biocompatibility.

In certain embodiments, the subject polymers are soluble in one or more common organic solvents for ease of fabrication and processing. Common organic solvents include such solvents as chloroform, dichloromethane, dichloroethane, 2-butanone, butyl acetate, ethyl butyrate, acetone, ethyl acetate, dimethylacetamide, N-methyl pyrrolidone, dimethylformamide, and dimethylsulfoxide.

5. Applications

A. Therapeutic Compositions

In part, a biocompatible polymer composition of the present invention includes a biocompatible and optionally biodegradable polymer, such as one having the recurring monomeric units shown in one of the foregoing formulas, optionally including any other biocompatible and optionally biodegradable polymer mentioned above or known in the art.

In addition to a lapachone or a prodrug thereof, the subject compositions may contain a "drug", "therapeutic agent," "medicament," or "bioactive substance," which are biologically, physiologically, or pharmacologically active substances that act locally or systemically in the human or animal body. For example, a subject composition may include any of the other compounds discussed above.

Various forms of the medicaments or biologically active materials may be used which are capable of being released from the polymer matrix into adjacent tissues or fluids. They may be acidic, basic, or salts. They may be neutral molecules, polar molecules, or molecular complexes capable of hydrogen bonding. They may be in the form of ethers, esters, amides and the like, including prodrugs which are biologically activated when injected into the human or animal body, e.g., by cleavage of an ester or amide. An analgesic agent is also an example of a "bioactive substance." Any additional bioactive substance in a subject composition may vary widely with the purpose for the composition. The term bioactive agent includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

Plasticizers and stabilizing agents known in the art may be incorporated in polymers of the present invention. In certain embodiments, additives such as plasticizers and stabilizing agents are selected for their biocompatibility. In certain embodiments, the additives are lung surfactants, such as 1,2-dipalmitoylphosphatidycholine (DPPC) and L-α-phosphatidylcholine (PC).

A composition of this invention may further contain one or more adjuvant substances, such as fillers, thickening agents or the like. In other embodiments, materials that serve as adjuvants may be associated with the polymer matrix. Such additional materials may affect the characteristics of the polymer matrix that results.

For example, fillers, such as bovine serum albumin (BSA) or mouse serum albumin (MSA), may be associated with the polymer matrix. In certain embodiments, the amount of filler may range from about 0.1 to about 50% or more by weight of the polymer matrix, or about 2.5, 5, 10, 25, or 40 percent. Incorporation of such fillers may affect the biodegradation of the polymeric material and/or the sustained release rate of any encapsulated substance. Other fillers known to those of skill in the art, such as carbohydrates, sugars, starches, saccharides, celluloses and polysaccbarides, including mannitose and sucrose, may be used in certain embodiments in the present invention.

In other embodiments, spheronization enhancers facilitate the production of subject polymeric matrices that are generally spherical in shape. Substances such as zein, microcrystalline cellulose or microcrystalline cellulose co-processed with sodium carboxymethyl cellulose may confer plasticity to the subject compositions as well as implant strength and integrity. In particular embodiments, during spheronization, extrudates that are rigid, but not plastic, result in the formation of dumbbell shaped implants and/or a high proportion of fines, and extrudates that are plastic, but not rigid, tend to agglomerate and form excessively large implants. In such embodiments, a balance between rigidity and plasticity is desirable. The percent of spheronization enhancer in a formulation typically range from 10 to 90% (w/w).

In certain embodiments, a subject composition includes an excipient. A particular excipient may be selected based on its melting point, solubility in a selected solvent (e.g., a solvent that dissolves the polymer and/or the therapeutic agent), and the resulting characteristics of the microparticles.

Excipients may comprise a few percent, about 5%, 10%, 15%, 20%, 25%, 30%, 40%, 50%, or higher percentage of the subject compositions.

Buffers, acids and bases may be incorporated in the subject compositions to adjust their pH. Agents to increase the diffusion distance of agents released from the polymer matrix may also be included.

Disintegrants are substances that, in the presence of liquid, promote the disruption of the subject compositions. Disintegrants are most often used in implants, in which the function of the disintegrant is to counteract or neutralize the effect of any binding materials used in the subject formulation. In general, the mechanism of disintegration involves moisture absorption and swelling by an insoluble material.

Examples of disintegrants include croscarmellose sodium and crospovidone which, in certain embodiments, may be incorporated into the polymeric matrices in the range of about 1–20% of total matrix weight. In other cases, soluble fillers such as sugars (mannitol and lactose) may also be added to facilitate disintegration of implants.

Other materials may be used to advantage to control the desired release rate of a therapeutic agent for a particular treatment protocol. For example, if the sustained release is too slow for a particular application, a pore-forming agent maybe added to generate additional pores in the matrix. Any biocompatible water-soluble material may be used as the pore-forming agent. They may be capable of dissolving, diffusing or dispersing out of the formed polymer system whereupon pores and microporous channels are generated in the system. The amount of pore-forming agent (and size of dispersed particles of such pore-forming agent, if appropriate) within the composition should affect the size and number of the pores in the polymer system.

Pore-forming agents include any pharmaceutically acceptable organic or inorganic substance that is substantially miscible in water and body fluids and will dissipate from the forming and formed matrix into aqueous medium or body fluids or water-immiscible substances that rapidly degrade to water-soluble substances.

Suitable pore-forming agents include, for example, sugars such as sucrose and dextrose, salts such as sodium chloride and sodium carbonate, and polymers such as hydroxylpropylcellulose, carboxymethylcellulose, polyethylene glycol, and PVP. The size and extent of the pores may be varied over a wide range by changing the molecular weight and percentage of pore-forming agent incorporated into the polymer system.

The charge, lipophilicity or hydrophilicity of any subject polymeric matrix may be modified by attaching in some fashion an appropriate compound to the surface of the matrix. For example, surfactants may be used to enhance wettability of poorly soluble or hydrophobic compositions. Examples of suitable surfactants include dextran, polysorbates and sodium lauryl sulfate. In general, surfactants are used in low concentrations, generally less than about 5%.

Binders are adhesive materials that may be incorporated in polymeric formulations to bind and maintain matrix integrity. Binders may be added as dry powder or as solution. Sugars and natural and synthetic polymers may act as binders.

Materials added specifically as binders are generally included in the range of about 0.5%–15% w/w of the matrix formulation. Certain materials, such as microcrystalline cellulose, also used as a spheronization enhancer, also have additional binding properties.

Various coatings may be applied to modify the properties of the matrices.

Three exemplary types of coatings are seal, gloss and enteric coatings. Other types of coatings having various dissolution or erosion properties may be used to further modify subject matrices behavior, and such coatings are readily known to one of ordinary skill in the art.

The seal coat may prevent excess moisture uptake by the matrices during the application of aqueous based enteric coatings. The gloss coat generally improves the handling of the finished matrices. Water-soluble materials such as hydroxypropylcellulose may be used to seal coat and gloss coat implants. The seal coat and gloss coat are generally sprayed onto the matrices until an increase in weight between about 0.5% and about 5%, often about 1% for a seal coat and about 3% for a gloss coat, has been obtained.

Enteric coatings consist of polymers which are insoluble in the low pH (less than 3.0) of the stomach, but are soluble in the elevated pH (greater than 4.0) of the small intestine. Polymers such as EUDRAGIT, RohmTech, Inc., Malden, Mass., and AQUATERIC, FMC Corp., Philadelphia, Pa., may be used and are layered as thin membranes onto the implants from aqueous solution or suspension or by a spray drying method. The enteric coat is generally sprayed to a weight increase of about one to about 30%, preferably about 10 to about 15% and may contain coating adjuvants such as plasticizers, surfactants, separating agents that reduce the tackiness of the implants during coating, and coating permeability adjusters.

The present compositions may additionally contain one or more optional additives such as fibrous reinforcement, colorants, perfumes, rubber modifiers, modifying agents, etc. In practice, each of these optional additives should be compatible with the resulting polymer and its intended use. Examples of suitable fibrous reinforcement include PGA microfibrils, collagen microfibrils, cellulosic microfibrils, and olefinic microfibrils. The amount of each of these optional additives employed in the composition is an amount necessary to achieve the desired effect.

B. Physical Structures of the Subject Compositions

The subject polymers may be formed in a variety of shapes. For example, in certain embodiments, subject polymer matrices may be presented in the form of microparticles or nanoparticles. Microspheres typically comprise a biodegradable polymer matrix incorporating a drug. Microspheres can be formed by a wide variety of techniques known to those of skill in the art. Examples of microsphere forming techniques include, but are not limited to, (a) phase separation by emulsification and subsequent organic solvent evaporation (including complex emulsion methods such as oil in water emulsions, water in oil emulsions and water-oil-water emulsions); (b) coacervation-phase separation; (c) melt dispersion; (d) interfacial deposition; (e) in situ polymerization; (f) spray drying and spray congealing; (g) air suspension coating; and (h) pan and spray coating. These methods, as well as properties and characteristics of microspheres are disclosed in, for example, U.S. Pat. Nos. 4,652,441; 5,100,669; 4,526,938; WO 93/24150; EPA 0258780 A2; U.S. Pat Nos. 4,438,253 and 5,330,768 the entire disclosures of which are incorporated by reference herein.

To prepare microspheres of the present invention, several methods can be employed depending upon the desired application of the delivery vehicles. Suitable methods include, but are not limited to, spray drying, freeze drying, air drying, vacuum drying, fluidized-bed drying, milling, co-precipitation and critical fluid extraction. In the case of spray drying, freeze drying, air drying, vacuum drying, fluidized-bed drying and critical fluid extraction; the components (stabilizing polyol, bioactive material, buffers, etc.) are first dissolved or suspended in aqueous conditions. In the case of milling, the components are mixed in the dried form and milled by any method known in the art. In the case of co-precipitation, the components are mixed in organic conditions and processed as described below. Spray drying can be used to load the stabilizing polyol with the bioactive material. The components are mixed under aqueous conditions and dried using precision nozzles to produce extremely uniform droplets in a drying chamber. Suitable spray drying machines include, but are not limited to, Buchi, NIRO, APV and Lab-plant spray driers used according to the manufacturer's instructions.

The shape of microparticles and nanoparticles may be determined by scanning electron microscopy. Spherically shaped nanoparticles are used in certain embodiments for circulation through the bloodstream. If desired, the particles may be fabricated using known techniques into other shapes that are more useful for a specific application.

In addition to intracellular delivery of a therapeutic agent, it also possible that particles of the subject compositions, such as microparticles or nanoparticles, may undergo endocytosis, thereby obtaining access to the cell. The frequency of such, an endocytosis process will likely depend on the size of any particle.

Microparticles may be administered by inhalation of a suitable composition using a suitable delivery device, such as an inhaler. This mode of administration may be used for local delivery to the lung and/or systemic delivery to the patient's bloodstream. Local administration of a lapachone in this fashion may be useful in the treatment or control of lung cancers, such a non-small cell lung cancer.

In other embodiments, polymeric formulations of lapachone are shaped as implantable drug delivery devices to delivery therapeutic agents to a localized tissue volume or mass. In certain embodiments, such devices are useful for treating a tumor, such as breast cancer, ovarian cancer, or prostate cancer. In certain exemplary embodiments, drug delivery devices are implanted into the breast, ovary, or prostate, or into the tissues immediately adjacent to the breast or prostate. The drug delivery devices, detailed below, release the lapachone and optionally additional therapeutic agents or drugs over time to treat the cancer, and/or symptoms associated with the cancer, or symptoms associated with other treatment modalities for the cancer. For example, dicoumarol can be incorporated in the implant(s) to alleviate some of the unwanted side effects induced by the lapachone.

According to one aspect of the invention, the polymeric implants are fashioned as spacers between brachytherapy seeds. Such spacers may, for example, be millirods, e.g., about 0.6 to about 1.0 mm in diameter, about 3–7 mm in length, preferably adapted to fit through a 19-gauge needle. Brachytherapy treatments can generate pain, edema, and associated voiding problems. In some embodiments, the brachytherapy drug delivery spacer includes a biologically active agent that decreases, and preferably eliminates, pain, swelling, and/or voiding symptoms following brachytherapy, and may also enhance (or be enhanced by) radiation therapy. Certain known therapeutic compounds, such as 5FU and triamcinolone acetonide, have beneficial effects in the treatment of these symptoms, especially in conjunction with brachytherapy.

Spacers may be placed between the radioactive seeds in the delivery needles of the brachytherapy machine, to keep the radioactive seeds in their proper predetermined positions. The simultaneous use of antiinflammatory agents that have a controlled and prolonged release rate also limits the brachytherapy side effects, while the localized delivery of the agents to the prostate does not impose the chemotherapeutic load on the patient's entire system that is a significant shortcoming of some prior systemic administration protocols.

In certain embodiments, solid articles useful in defining shape and providing rigidity and structural strength to the polymeric matrices may be used. For example, a polymer may be formed on a mesh or other weave for implantation. A polymer may also be fabricated as a stent or as a shunt, adapted for holding open areas within body tissues or for draining fluid from one body cavity or body lumen into another. Further, a polymer may be fabricated as a drain or a tube suitable for removing fluid from a post-operative site, and in some embodiments adaptable for use with closed section drainage systems such as Jackson-Pratt drains and the like as are familiar in the art.

The mechanical properties of the polymer may be important for the processability of making molded or pressed articles for implantation. For example, the glass transition temperature may vary widely but must be sufficiently lower than the temperature of decomposition to accommodate conventional fabrication techniques, such, as compression molding, extrusion, or injection molding.

C. Biodegradability and Release Characteristics

In certain embodiments, the formulations of the present invention, upon contact with body fluids, undergo gradual degradation. The life of a biodegradable polymer in vivo depends upon, among other things, its molecular weight, crystallinity, biostability, and the degree of crosslinking. In general, the greater the molecular weight, the higher the degree of crystallinity, and the greater the biostability, the slower biodegradation will be.

If a subject composition is formulated with a therapeutic agent or other material, release of such an agent or other material for a sustained or extended period as compared to the release from an isotonic saline solution generally results. Such release profile may result in prolonged delivery (over, say 1 to about 2,000 hours, or alternatively about 2 to about 800 hours) of effective amounts (e.g., about 0.0001 mg/kg/hour to about 10 mg/kg/hour) of the agent or any other material associated with the polymer.

A variety of factors may affect the desired rate of hydrolysis of polymers of the subject invention, the desired softness and flexibility of the resulting solid matrix, rate and extent of bioactive material release. Some of these factors include the selection/identity of the various subunits, the enantiomeric or diastereomeric purity of the monomeric subunits, homogeneity of subunits found in the polymer, and the length of the polymer. For instance, the present invention contemplates heteropolymers with varying linkages, and/or the inclusion of other monomeric elements in the polymer, in order to control, for example, the rate of biodegradation of the matrix.

To illustrate further, a wide range of degradation rates may be obtained by adjusting the hydrophobicities of the backbones or side chains of the polymers while still maintaining sufficient biodegradability for the use intended for any such polymer. Such a result may be achieved by varying the various functional groups of the polymer. For example, the combination of a hydrophobic backbone and a hydrophilic linkage produces heterogeneous degradation because cleavage is encouraged whereas water penetration is resisted.

One protocol generally accepted in the field that may be used to determine the release rate of any therapeutic agent or other material loaded in the polymer matrices of the present invention involves degradation of any such matrix in a 0.1 M PBS solution (pH 7.4) at 37° C., an assay known in the art. For purposes of the present invention, the term "PBS protocol" is used herein to refer to such a protocol.

In certain instances, the release rates of different polymer systems of the present invention may be compared by subjecting them to such a protocol. In certain instances, it may be necessary to process polymeric systems in the same fashion to allow direct and relatively accurate comparisons of different systems to be made. For example, the present invention teaches several different means of formulating the polymeric, matrices of the present invention. Such comparisons may indicate that anyone polymeric system releases incorporated material at a rate from about 2 or less to about 1000 or more times faster than another polymeric system.

Alternatively, a comparison may reveal a rate difference of about 3, 5, 7, 10, 25, 50, 100, 250, 500 or 750 times. Even higher rate differences are contemplated by the present invention and release rate protocols.

In certain embodiments, when formulated in a certain manner, the release rate for polymer systems of the present invention may present as mono- or bi-phasic.

Release of any material incorporated into the polymer matrix, which is often provided as a microsphere, may be characterized in certain instances by an initial increased release rate, which may release from about 5 to about 50% or more of any incorporated material, or alternatively about 10, 15, 20, 25, 30 or 40%, followed by a release rate of lesser magnitude.

The release rate of any incorporated material may also be characterized by the amount of such material released per day per mg of polymer matrix. For example, in certain embodiments, the release rate may vary from about 1 ng or less of any incorporated material per day per mg of polymeric system to about 500 or more ng/day/mg. Alternatively, the release rate may be about 0.05, 0.5, 5, 10, 25, 50, 75, 100, 125, 150, 175, 200, 250, 300, 350, 400, 450, or 500 ng/day/mg. In still other embodiments, the release rate of any incorporated material may be 10,000 ng/day/mg, or even higher. In certain instances, materials incorporated and characterized by such release rate protocols may include therapeutic agents, fillers, and other substances.

In another aspect, the rate of release of any material from any polymer matrix of the present invention may be presented as the half-life of such material in the matrix.

In addition to the embodiment involving protocols for in vitro determination of release rates, in vivo protocols, whereby in certain instances release rates for polymeric systems may be determined in vivo, are also contemplated by the present invention. Other assays useful for determining the release of any material from the polymers of the present system are known in the art.

D. Implants and Delivery Systems

In its simplest form, a biodegradable delivery system for a therapeutic agent consists of a dispersion or solution of a lapachone, optionally together with one or more other therapeutic agents, in a polymer matrix. In other embodiments, an article is used for implantation, injection, or otherwise placed totally or partially within the body, the article comprising the subject compositions. It is particularly important that such an article result in minimal tissue irritation when implanted or injected into vasculated tissue.

Biodegradable delivery systems, and articles thereof, may be prepared in a variety of ways known in the art. The polymer or composition may be melt-processed using conventional extrusion or injection molding techniques, or these products may be prepared by dissolving in an appropriate solvent, followed by formation of the device, and subsequent removal of the solvent by evaporation or extraction.

Once a system or implant article is in place, it should remain in at least partial contact with a biological fluid, such as blood, internal organ secretions, mucus membranes, cerebrospinal fluid, and the like to allow for sustained release of any encapsulated therapeutic agent.

6. Dosages and Formulations of the Subject Compositions

In most embodiments, the subject polymers will incorporate the lapachone or other therapeutic agent in an amount sufficient to deliver to a patient a therapeutically effective amount as part of a prophylactic or therapeutic treatment. The desired concentration of active compound in the particle will depend on absorption, inactivation, and excretion rates of the drug as well as the delivery rate of the compound from the subject compositions. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

Further, the amounts of bioactive substances will vary depending upon the relative potency of the agents selected. Additionally, the optimal concentration and/or quantities or amounts of any particular therapeutic agent may be adjusted to accommodate variations in the treatment parameters. Such treatment parameters include the polymer composition of a particular microsphere preparation, the identity of the therapeutic agent utilized, and the clinical use to which the preparation is put, e.g., the site treated, the type of patient, e.g., human or non-human, adult or child, and the nature of the disease or condition.

The concentration and/or amount of any therapeutic agent or other encapsulated material for a given subject composition may readily identified by routine screening in animals, e.g., rats, by screening a range of concentration and/or amounts of the material in question using appropriate assays. Known methods are also available to assay local tissue concentrations, diffusion rates from microspheres and local blood flow before and after administration of therapeutic formulations according to the invention. One such method is microdialysis, as reviewed by T. E. Robinson et al., 1991, MICRODIALYSIS IN THE NEUROSCIENCES, Techniques, volume 7, Chapter 1. The methods reviewed by Robinson may be applied, in brief, as follows. A microdialysis loop is placed in situ in a test animal. Dialysis fluid is pumped through the loop. When microspheres according to the invention are injected adjacent to the loop, released drugs are collected in the dialysate in proportion to their local tissue concentrations. The progress of diffusion of the active agents may be determined thereby with suitable calibration procedures using known concentrations of active agents.

In certain embodiments, the dosage of the subject invention may be determined by reference to the plasma concentrations of the therapeutic agent or other encapsulated materials. For example, the maximum plasma concentration ($C_{max}$) and the area under the plasma concentration-time curve from time 0 to infinity may be used.

The polymers of the present invention may be administered by various means, depending on their intended use, as is well known in the art. For example, if subject compositions are to be administered orally, it may be formulated as tablets, capsules, granules, powders or syrups. Alternatively, formulations of the present invention may be administered parenterally as injections (intravenous, intramuscular, or subcutaneous), drop infusion preparations, or suppositories. For application by the ophthalmic mucous membrane route, subject compositions may be formulated as eyedrops or eye ointments. These formulations may be prepared by conventional means, and, if desired, the subject compositions may be mixed with any conventional additive, such as a binder, a disintegrating agent, a lubricant, a corrigent, a solubilizing agent, a suspension aid, an emulsifying agent or a coating agent.

In addition, in certain embodiments, subject compositions of the present invention maybe lyophilized or subjected to another appropriate drying technique such as spray drying.

The subject compositions may be administered once, or may be divided into a number of smaller doses to be administered at varying intervals of time, depending in part on the release rate of the compositions and the desired dosage.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of a subject composition which may be combined with a carrier material to produce a single dose vary depending upon the subject being treated, and the particular mode of administration.

Methods of preparing these formulations or compositions include the step of bringing into association subject compositions with the carrier and, optionally, one or more accessory ingredients. In general, the formulations are prepared by uniformly and intimately bringing into association a subject composition with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition as an active ingredient. Subject compositions of the present invention may also be administered as a bolus, electuary, or paste.

In solid dosage forms for oral administration (capsules, tablets, pills, dragees, powders, granules and the like), the subject composition is mixed with one or more pharmaceutically acceptable carriers and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof, and (10) coloring agents. In the case of capsules, tablets and pills, the pharmaceutical compositions may also comprise buffering agents. Solid compositions of a similar type may also be employed as fillers in soft and hard-filled gelatin capsules using lactose or milk sugars, as well as high molecular weight polyethylene glycols and the like.

A tablet may be made by compression or molding, optionally with one or more accessory ingredients. Compressed tablets may be prepared using a binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject compositions, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, peanut, sunflower, soybean, olive, castor, and sesame oils), glycerol, tetrahydrofuryl alcohol, polyethylene glycols and fatty acid esters of sorbitan, and mixtures thereof.

Suspensions, in addition to the subject compositions, may contain suspending agents as, for example, ethoxylated isostearyl alcohols, polyoxyethylene sorbitol, and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating carriers comprising, for example, cocoa butter, polyethylene glycol, a suppository wax, or a salicylate, and which is solid at room temperature, but liquid at body temperature and, therefore, will melt in the appropriate body cavity and release the encapsulated therapeutic agent.

Formulations which are suitable for vaginal administration also include pessaries, tampons, creams, gels, pastes, foams, or spray formulations containing such carriers as are known in the art to be appropriate.

Dosage forms for transdermal administration include powders, sprays, ointments, pastes, creams, lotions, gels, solutions, patches, and inhalants. A subject composition may be mixed under sterile conditions with a pharmaceutically acceptable carrier, and with any preservatives, buffers, or propellants that may be required. For transdermal administration, the complexes may include lipophilic and hydrophilic groups to achieve the desired water solubility and transport properties.

The ointments, pastes, creams and gels may contain, in addition to subject compositions, other carriers, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays may contain, in addition to a subject composition, excipients such as lactose, talc, silicic acid, aluminum hydroxide, calcium silicates and polyamide powder, or mixtures of such substances. Sprays may additionally contain customary propellants, such as chlorofluorohydrocarbons and volatile unsubstituted hydrocarbons, such as butane and propane.

Microspheres which may be administered in inhalant or aerosol formulations according to the invention include agents, such as adjuvants, diagnostic agents, imaging agents, or therapeutic agents useful in inhalation therapy, which may be presented in a form which is soluble or substantially soluble in the selected propellant system.

The particle size of the particulate medicament should be such as to permit inhalation of substantially all of the medicament into the lungs upon administration of the aerosol formulation and will thus desirably be less than 20 microns, preferably in the range 1 to 10 microns, e.g., 1 to 5 microns. The particle size of the medicament may be reduced by conventional means, for example by milling or micronisation.

The final aerosol formulation desirably contains 0.005–10% w/w, preferably 0.005–5% w/w, especially 0.01–1.0% w/w, of medicament relative to the total weight of the formulation.

It is desirable, but by no means required, that the formulations of the invention contain no components which may provoke the degradation of stratospheric ozone. In particular it is desirable that the formulations are substantially free of chlorofluorocarbons such as $CCl_3F$, $CCl_2F_2$ and $CF_3CCl_3$. As used herein "substantially free" means less than 1% w/w based upon the propellant system, in particular less than 0.5%, for example 0.1% or less.

The propellant may optionally contain an adjuvant having a higher polarity and/or a higher boiling point than the propellant. Polar adjuvants which may be used include (e.g., $C_{2-6}$) aliphatic alcohols and polyols such as ethanol, isopropanol and propylene glycol, preferably ethanol. In general only small quantities of polar adjuvants (e.g., 0.05–3.0% w/w) may be required to improve the stability of the dispersion—the use of quantities in excess of 5% w/w may tend to dissolve the medicament. Formulations in accordance with the invention may preferably contain less than 1% w/w, e.g. about 0.1% w/w, of polar adjuvant. However, the formulations of the invention are preferably substantially free of polar adjuvants, especially ethanol. Suitable volatile adjuvants include saturated hydrocarbons such as propane, n-butane, isobutane, pentane and isopentane and alkyl ethers such as dimethyl ether. In general, up to 50% w/w of the propellant may comprise a volatile adjuvant, for example 1 to 30% w/w of a volatile saturated C1–C6 hydrocarbon.

Optionally, the aerosol formulations according to the invention may further comprise one or more surfactants. The surfactants must be physiologically acceptable upon administration by inhalation. Within this category are included surfactants such as L-α-phosphatidylcholine(PC), 1,2-dipalmitoylphosphatidycholine(DPPC), oleic acid, sorbitan trioleate, sorbitan mono-oleate, sorbitan monolaurate, polyoxycthylene(20)sorbitan monolaurate, polyoxyethylene (20)sorbitan monooleate, natural lecithin, oleyl polyoxyethylene(2)ether, stearyl polyoxyethylene(2)ether, lauryl polyoxyethylene(4)ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil, and sunflower seed oil. Preferred surfactants are lecithin, oleic acid, and sorbitan trioleate.

If desired, the surfactant may be incorporated into the aerosol formulation in the form of a surface coating on the particulate medicament. In this case, the use of substantially non-ionic surfactants which have reasonable solubility in substantially non-polar solvents is frequently advantageous since it facilitates coating of the medicament particles using solutions of surfactants in non-polar solvents in which the medicament has limited or minimal solubility.

The amount of surfactant employed in coating the particulate medicament is desirably in the range 0.1 to 10% w/w preferably 1 to 10% w/w, relative to the medicament. Where the surfactant is present as a surface coating, the amount may advantageously be chosen such that a substantially monomolecular coating of sent is formed. However, it is preferable that the formulations of the invention are substantially free of surfactants, i.e., contain less than an effective stabilizing amount of a surfactant such as less than 0.0001% by weight of medicament.

The formulations of the invention may be prepared by dispersal of the medicament in the selected propellant and/or co-propellant in an appropriate container, e.g., with the aid of sonication. Preferably the particulate medicament is suspended in co-propellant and filled into, a suitable container. The valve of the container is then sealed into place and the propellant introduced by pressure filling through the valve in the conventional manner. The active ingredient may be thus suspended or dissolved in a liquified propellant, sealed in a container with a metering valve and fitted into an actuator. Such metered dose inhalers are well known in the art. The metering valve may meter 10 to 500 μL and preferably 25 to 150 μL. In certain embodiments, dispersal may be achieved using dry powder inhalers (e.g., spinhaler) for the microspheres (which remain as dry powders). In other embodiments, nanospheres, may be suspended in an aqueous fluid and nebulized into fine droplets to be aerosolized into the lungs.

Sonic nebulizers may be used because they minimize exposing the agent to shear, which may result in degradation of the compound. Ordinarily, an aqueous aerosol is made by formulating an aqueous solution or suspension of the polymeric materials together with conventional pharmaceutically acceptable carriers and stabilizers. The carriers and stabilizers vary with the requirements of the particular compound, but typically include non-ionic surfactants (Tweens, Pluronics, or polyethylene glycol), innocuous proteins like serum albumin, sorbitan esters, oleic acid, lecithin, amino acids such as glycine, buffers, salts, sugars, or sugar alcohols. Aerosols generally are prepared from isotonic solutions.

Ophthalmic formulations, eye ointments, powders, solutions and the like, are also contemplated as being within the scope of this invention.

Certain pharmaceutical compositions of this invention suitable for parenteral administration comprise one or more subject compositions in combination with one or more pharmaceutically acceptable sterile isotonic; aqueous or non-aqueous solutions, dispersions, suspensions or emulsions, or sterile powders which may be-reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

Microsphere and/or nanosphere compositions may be suspended in a pharmaceutically acceptable solution, such as saline, Ringer's solution, dextran solution, dextrose solution, sorbitol solution, a solution containing polyvinyl alcohol (from about 1% to about 3%, preferably about 2%), or an osmotically balanced solution comprising a surfactant (such as Tween 80 or Tween 20) and a viscosity-enhancing agent (such as gelatin, alginate, sodium carboxymethylcellulose, etc.). In certain embodiments, the composition is administered subcutaneously. In other embodiments, the composition is administered intravenously. For intravenous delivery, the composition is preferably formulated as microspheres or nanospheres on average less than about 15 microns, more particularly less than about 10 microns, and still more particularly less than about 5 microns in average diameter.

Exemplification

The invention now being generally described, it will be more readily understood by reference to the following examples, which are included merely for purposes of illustration of certain aspects and embodiments of the present invention, and are not intended to limit the invention.

1. Enhancement of Solubility and Bioavailability of β-Lapachone Using Cyclodextrin Inclusion Complexes Materials and Methods Materials α-CD, β-CD, γ-CD and HPβ-CD were obtained from Cyclodextrin Technologies Development, Inc. (CTD) (High Springs, Fla.) with >98% purity. β-Lap was synthesized following a previously reported procedure (S. M. Planchon, S. Wuerzberger, B. Frydman, D. T. Witiak, P. Hutson, D. R. Church, G. Wilding and D. A. Boothman. Cancer Res. 55(17):3706–3711 (1995)). Phosphate-buffered saline (PBS, pH=7.4) was purchased from Fisher Scientific (Pittsburg, Pa.). RPMI 1640 medium, fetal bovine serum, L-glutamine, penicillin and streptomycin were purchased from Hyclone (Logan, Utah) and Life Technologies, Inc. (Rockville, Md.). MCF-7 breast cancer cells were routinely passed at 1:5–1:20 dilutions every five days using mycoplasma-free 0.05% trypsin as described (J. J. Pink, S. M. Planshon, C. Tagliarino, S. M. Wuerzberger-Davis, M. E. Varnes, D. Siegel and D. A. Boothman. J Biol Chem. 275:5416–5424 (2000)).

Phase Solubility Studies of CD-β-lap Inclusion Complexes

Solubility studies were performed by adding excess amount of β-lap to a series of PBS buffer that contain different concentrations of each CD molecule ranging from zero to its solubility limit (see Table 1 for the solubility limit of each CD molecule). A schematic diagram of the intermolecular interactions and their effect on solubility is provided as FIG. 1. The suspensions were stirred at 25° C. until dissolution equilibrium was reached. Then aliquots were withdrawn, filtered (Nylon syringe filter 0.2 μm pore size from Fisher Scientific (Pittsburg, Pa.)) and analyzed for β-lap concentrations by UV-V is spectrophotometry ($\lambda_{max}$= 257.2 nm, $\epsilon$=109.6 ml/(mg·cm)). Phase solubility diagram for each CD was obtained by plotting the β-lap solubility at dissolution equilibrium as a function of the CD concentration. The association constant ($K_c$)

$$K_c = \frac{\text{Slope}}{\text{Y-intercept } x(1 - \text{Slope})} \quad (1)$$

for the complex formation was calculated based on Equation 1 assuming a 1:1 ratio of complex formation (T. Higuchi and K. A. Connors. Adv Anal Chem Instrum. 4:117–212 (1965)).

$^1$H NMR Study of CD.β-lap Inclusion Complexes

All $^1$H NMR spectra were obtained on a Varian 600 MHz NMR spectrometer. The probe temperature was set at 25° C. $^1$H-NMR spectrum of β-lap was assigned by homonuclear correlation spectoscopy (COSY) and heteronuclear multiple quantum coherence spectroscopy (HMBC). One dimensional gradient-enhanced ROESY (GROESY) experiments were carried out by using the following pulse sequence; relaxation delay=1 s, 90° pulse width=8.2 μs, spin lock time=400 ms and the acquisition time=3.495 s. The concentrations of β-lap and HPβ-CD for the GROESY experiments were 10.6 and 58.8 mM in D$_2$O, respectively.

The complex for the NMR shift titration study was prepared by adding 78 μl of β-lap stock solution (1.64 mM in MeOH). The solution was dried and then variable amounts of β-CD and HPβ-CD solution in D$_2$O were added. The resulting β-lap (0.123 mM) and β-CD (0.1–14.7 mM) or HPβ-CD (0.5–430 mM) solutions were vigorously stirred at 25° C. overnight to ensure the reaching of equilibrium. The association constants can be determined based on Equation 2 (A. Botsi, K. Yannakopoulou, B. Perly and E. Hadjoudis, J Org Chem. 60: 4017–4023 (1995)).

$$\Delta\delta_{Hc \text{ or } Hd} = \frac{K_C \Delta\delta_0 (\Delta\delta_0 [CD] - \Delta\delta[\beta\text{-Lap}])}{\Delta\delta_0 + K_C (\Delta\delta_0 [CD] - \Delta\delta[\beta\text{-Lap}])} \quad (2)$$

For methyl protons (Hc) on β-lap, $\Delta\delta_{Hc}$ denotes the difference of chemical shift between the two splitting methyl groups at a particular concentration of CD. For aromatic Hd protons, $\Delta\delta_{Hd}$ ($\Delta\delta_{Hd}$=7.787-$\delta_i$) is calculated as the difference between the chemical shift of pure β-lap (7.787 ppm) from that of CD.β-lap inclusion complex at a particular concentration of CD ($\delta_i$). For both Hc and Hd protons, $\Delta\delta_0$ denotes the difference between pure β-lap and pure CD.β-lap inclusion complexes, [CD] stands for the concentration of cyclodextrin and [β-lap] denotes the concentration of β-lap used in this experiment (0.123 mM).

Fluorescence Study of CD.β-lap Inclusion Complexes

A fluorescence study was preformed on a LS45 Luminescence Spectrometer (Perkin Elmer Instruments) with 100 nm/min scan speed and 10 nm for both excitation and emission slit widths. Initially, emission spectra of β-lap (0.015 mg/ml) in PBS buffer were obtained at different excitation wavelengths to determine the optimal values of $\lambda_{ex}$ and $\lambda_{em}$ for spectrophotometry measurements. The effect of CD concentrations on the fluorescence spectra of β-lap was studied. In these studies, each sample was prepared by adding the same volume (4 ml) of a stock solution of β-lap (0.005 mg/ml) but different quantities of CD inside a 5 ml volumetric flask filled with PBS buffer. The resulting solutions were vigorously stirred at 25° C. overnight to ensure the reaching of equilibrium. Emission spectra of β-lap at different CD concentrations were obtained at $\lambda_{ex}$=330 nm. The fluorescence intensity at $\lambda_{em}$=436 nm was measured and used to determine the value of $K_c$ of CD.β-lap inclusion complex.

In Vitro Cytotoxicity Assays

The cytotoxicity of β-CD.β-lap and HPβ-CD.β-lap inclusion complexes to MCF-7 breast cancer cells was determined following a previously published procedure (16). The MCF-7 cells were grown in RPMI 1640 medium supplemented with 5% fetal bovine serum, 2 mM L-glutamine, 100 units/ml penicillin, and 100 mg/ml streptomycin. In cytotoxicity studies, cells were first seeded into ninety-six well plates at $1 \times 10^4$ cells/well in 1 ml medium and allowed to attach overnight. Media were removed 24 h later, and new medium (1 ml) containing different concentrations of CD alone or β-lap in CD inclusion complex were added to each well. After 4 h, the media were removed and replaced with drug-free growth media. Cells were allowed to grow for an additional 6 days. On day 7, cells were washed with PBS after media removal, and 250 μl double distilled Milli Q $H_2O$ was added to each well. After one freeze-thaw cycle, TNE buffer (2 M NaCl, 1 mM EDTA, 10 mM Tris-HCl, pH 7.4) with 10 μg/ml Hoechst 33258 (Sigma) fluorescent dye was added to each well. Changes in cell number, measured as DNA content, were then determined by an adaptation of the method of Labarca and Paigen (C. Labarca and K. Paigen. *Anal Biochem.* 102:344–352 (1980)) and analyzed with a Perkin Elmer HTS 7000 Bio Assay Reader with excitation wavelength of 360 nm and emission wavelength of 460 nm. Data were expressed as relative growth (T/C) by dividing DNA content of treated cells (T) by that of untreated cells (C) at identical times. The reproducibility of each data point is represented by the means, +/− SEM, from at least six replicate wells. β-Lap in dimethylsulfoxide (DMSO) was used as a positive control to compare the drug cytotoxicity to MCF-7 cells.

Animal Toxicity Studies

C57Blk/6 female mice (3–4 week-old, 18–20 g) (Jackson Labs, Me.) were used to study the morbidity and mortality of mice treated with HPβ-CD.β-lap inclusion complex. Four mice per group were used for each dose, which varied from 20 to 100 mg/kg. Two groups of four mice were used for 60 mg/kg, since this dose proved to be near the $LD_{50}$ (lethal dose that kills 50% of the mice population) of the β-lap in HPβ-CD inclusion complex. Mice were injected (i.p.) every Monday, Wednesday and Friday for three weeks for a total of 10 injections. Control animals (4 mice/group) were injected with 5000 mg/kg of HPβ-CD alone to evaluate its toxicity. This HPβ-CD dose is approximately ten times of the HPβ-CD amount introduced at the highest dose of β-lap (100 mg/kg) via the HPβ-CD.β-lap inclusion complex. The higher dose of HPβ-CD was used to ensure the lack of toxicity of this compound. Weight and lethality were measured on a daily basis following initial drug administration. All animals were maintained in a facility accredited by the Association for Assessment and Accreditation of Laboratory Animal Care according to the "Principles of Laboratory Animal Care" of the National Institutes of Health.

Results and Discussion

Solubility Study

Figure 2A:
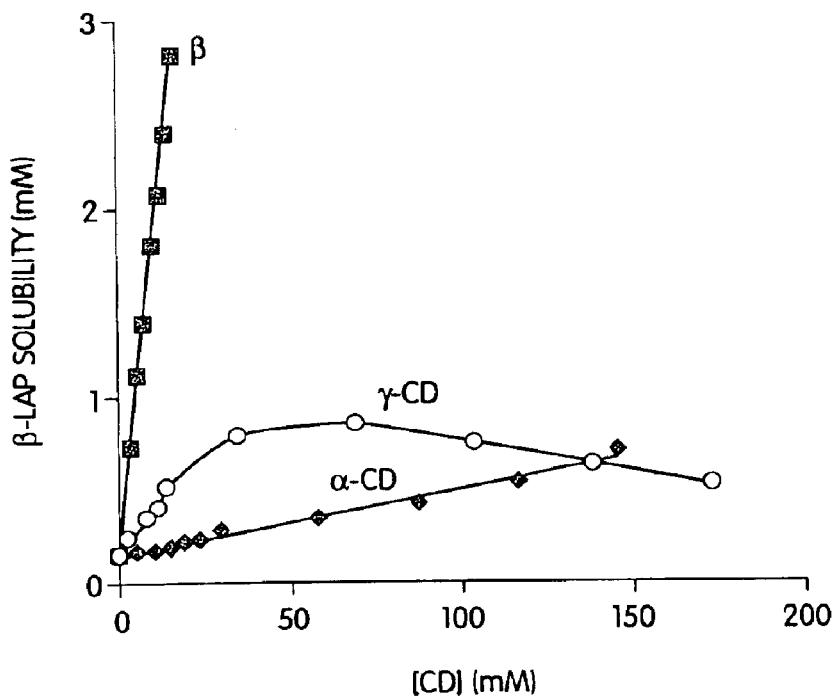
FIG. 2. Phase solubility diagrams of β-lap as a function of cyclodextrin concentrations at 25° C. A) α-CD, β-CD and γ-CD. B) HPβ-CD.
Figure 2B:
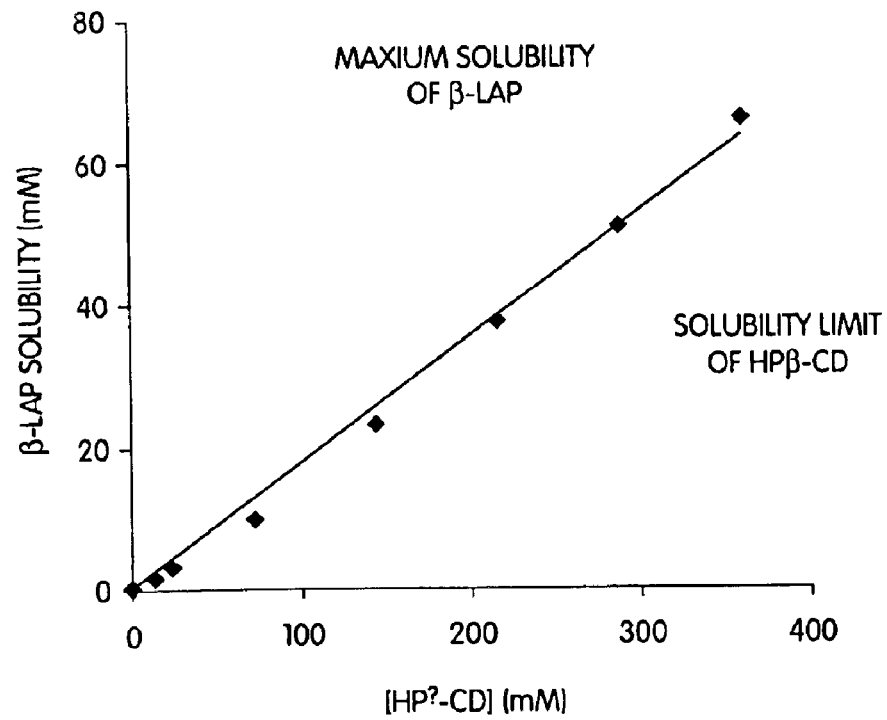

The effect of cyclodextrins on the aqueous solubility of β-lap was evaluated using the phase solubility method (T. Higuchi and K. A. Connors. *Adv Anal Chem Instrum.* 4:117–212 (1965)). FIG. 2 shows the phase diagrams of β-lap with four different types of CDs in PBS buffer. The solubility of β-lap increased linearly as a function of α-, β-, or HPβ-CD concentrations. These phase diagrams are classified as type $A_L$ by Higuchi, which denotes a linear increase in solubility. In contrast, γ-CD showed a typical $B_S$-type solubility curve, which denotes an initial rise in the solubility of the solute followed by a plateau and decreased region due to the limited solubility of the complexes.

Increases in β-lap solubility in aqueous CD solutions are consistent with the formation of inclusion complexes between β-lap and CD molecules. In general, the main driving force for the complex formation is the hydrophobic interactions between a poorly soluble guest compound, such as β-lap, and the a polar cavity of the CD molecule. The hydrophobicity and geometry of the guest molecule as well as the cavity size of the CD molecule are important parameters for the complex formation. In the current study, the enhancement of β-lap solubility is highly dependent on the type of CD molecule. For example, the phase diagram for β-CD shows a much higher slope (0.16) than that of α-CD (0.0035) and the linear region ([γ-CD]<20 mM) of γ-CD (0.024, FIG. 2A), demonstrating that β-CD is more effective to solubilize β-lap. Based on the phase solubility diagrams, the association constants for the different inclusion complexes are determined using Equation 1. The values of $K_c$ are 20.0±0.7, (1.23±0.01)×10³, (0.94±0.08)×10³ and 160±5 $M^{-1}$ for α-CD, β-CD, HPβ-CD, and γ-CD, respectively.

The different association constants for different cyclodextrin molecules indicate the importance of cavity size to encapsulate the β-lap molecule. α-CD has the lowest affinity to associate with β-lap, presumably because β-lap cannot fit into the relatively small hydrophobic cavity of α-CD (diameter ~5 Å, Table 1). This is in agreement with other studies (M. V. Rekharsky and Y. Inoue. *Chem Rev.* 98:1875–1917 (1998)) in which guest molecules carried a phenyl moiety. On the other hand, although the wider cavity size of γ-CD (diameter ~8 Å) allows room for encapsulation ($K_c$ increased by a factor of 8 for γ-CD over α-CD), it has lower affinity to associate with β-lap than that of β-CD and HPβ-CD, which have smaller cavity size. Therefore, β-CD and HPβ-CD appear to be significantly better host molecules for β-lap encapsulation. The much higher association constants of HPβ-CD and β-CD show the importance of appropriate cavity size in facilitating the interactions between β-lap and HPβ-CD or β-CD, as further supported by molecular recognition studies of host-guest chemistry (K. A. Connors. *Chem Rev.* 97:1325–1357 (1997)).

Even though β-CD is a better host molecule for β-lap than α-CD and γ-CD, its application to maximize the solubility of β-lap is limited by the solubility of β-CD vehicle itself (16.3 mM). Consequently, the maximal solubility of β-lap in β-CD solution is limited to 2.8 mM or 0.68 mg/ml. This concentration is still relatively low for systemic administrations of this drug. To overcome this problem, we used HPβ-CD molecule as a β-lap carrier. HPβ-CD is formed by covalent modification of the external hydroxyl groups on β-CD by hydroxylpropyl groups. The modification significantly increased the solubility limit of HPβ-CD (360 mM, a factor of 22 over β-CD). The maximal solubility of β-lap in HPβ-CD solution reached 66.0 mM or 16.0 mg/ml, a 24-fold increase over that in β-CD vehicle and a 413-fold increase over β-lap aqueous solubility (0.16 mM). HPβ-CD provides the most effective solubilization of β-lap.

NMR Study of CD.β-Lap Inclusion Complexes

Figure 3A:
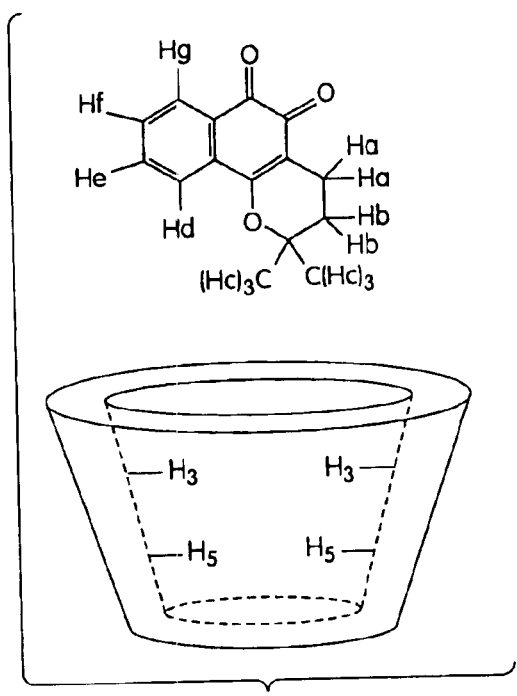
FIG. 3. (A) Chemical structure of β-lap and general geometry of HPβ-CD; (B) GROESY spectra of HPβ-CD.β-lap inclusion complex in $D_2O$ at 25° C.; (C) the $^1H$ NMR spectrum of HPβ-CD.β-lap inclusion complex. The concentrations of HPβ-CD and β-lap are 58.8 and 10.6 mM, respectively.
Figure 3B:
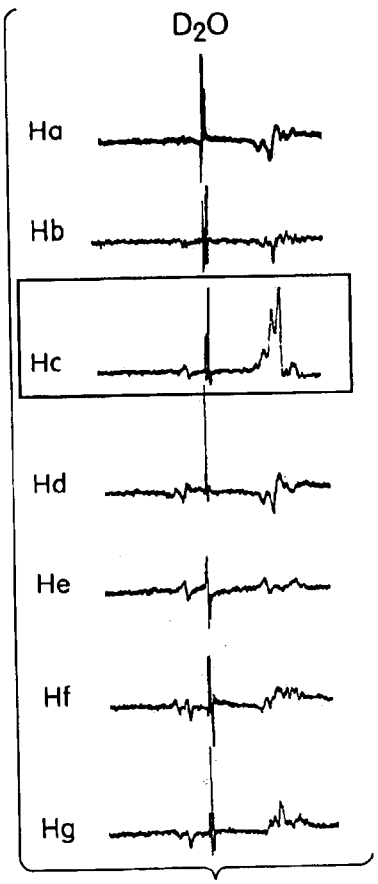
Figure 3C:

NMR spectroscopy is a powerful tool to study the inclusion phenomena. It has been shown that GROESY spectroscopy can be used to accurately detect the nuclear overhauser effect (NOE) (P. Adell, T. Parella, F. Sanchez-Ferrando and A. Virgili. *J Magn Reson.* 108: 77–80 (1995); Y. Ikeda, S. Motoune, T. Matsuoka, H. Arima, F. Hirayama and K. Uekama. *J Pharm Sci.* 91(11): 2390–2398 (2002)). In this study, we carried out the GROESY experiment to gain insight regarding the molecular structure of HPβ-CD.β-lap inclusion complex. FIG. 3 shows the GROESY spectra of the HPβ-CD.β-lap inclusion complex obtained by exciting every proton of β-lap (Ha to Hg). The significant NOE enhancement of the H5 and H3 protons located inside the HPβ-CD cavity was observed with the selective excitation of the Hc protons from β-lap. In contrast, no obvious NOE enhancement was observed with the selective excitation of the rest of β-lap protons, suggesting that the methyl moiety of β-lap is bound inside the cavity. This result also suggests that HPβ-CD forms a 1:1 inclusion complex with β-lap.

Figure 4A:
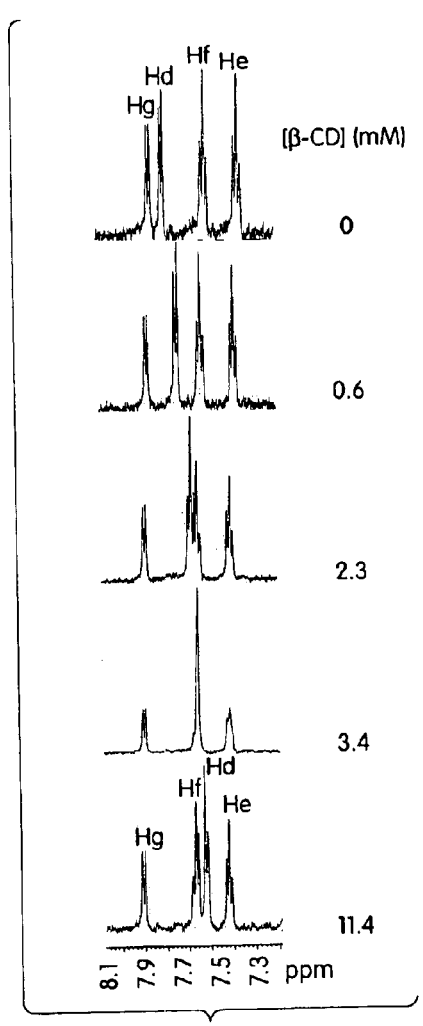
FIG. 4. $^1H$ NMR (600 MHz) spectra of β-lap ([β-lap]= 0.123 mM) as a function of β-CD concentrations in $D_2O$: (A) phenyl protons (Hd, He, Hf and Hg); (B) methyl and methylene protons (Ha, Hb and Hc).
Figure 4B:
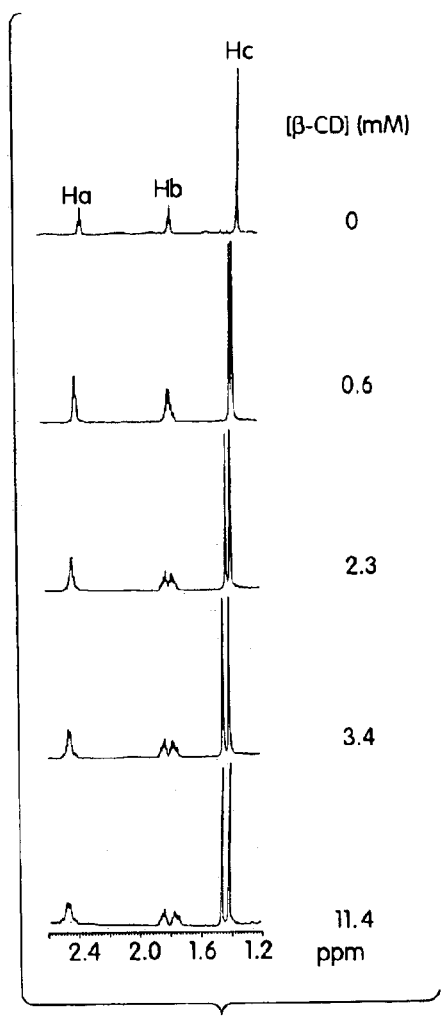

It is well known that the insertion of a guest molecule into the hydrophobic cavity of cyclodextrin can affect chemical shifts of the guest protons. In this experiment, we studied the effect of β-CD and HPβ-CD on the resonance of β-lap protons. FIG. 4A shows the effect of increasing β-CD concentration on the $^1$H NMR spectra of phenyl protons of β-lap. Interestingly, Hd was the only proton that showed upfield shifts as a result of increasing β-CD concentrations. Above [β-CD]=11.4 mM, no further changes of the upfield shift were observed (data not shown). The upfield shifts of Hd as a result of increasing of HPβ-CD concentrations were also found. FIG. 4B shows the effect of β-CD on the $^1$H NMR spectra of methyl (Hc) and methylene (Ha, Hb) protons of β-lap. A splitting of these three groups of proton peaks was observed due to the formation of inclusion complex. This effect was most pronounced with the methyl protons (Hc) whereas Ha protons had the least effect, suggesting the formation of diastereomeric complexes between β-lap and CD. A splitting of Ha, Hb and Hc was also found with HPβ-CD, but the signal was interfered with by the methylene protons from hydroxypropyl groups on HPβ-CD.

Figure 5:
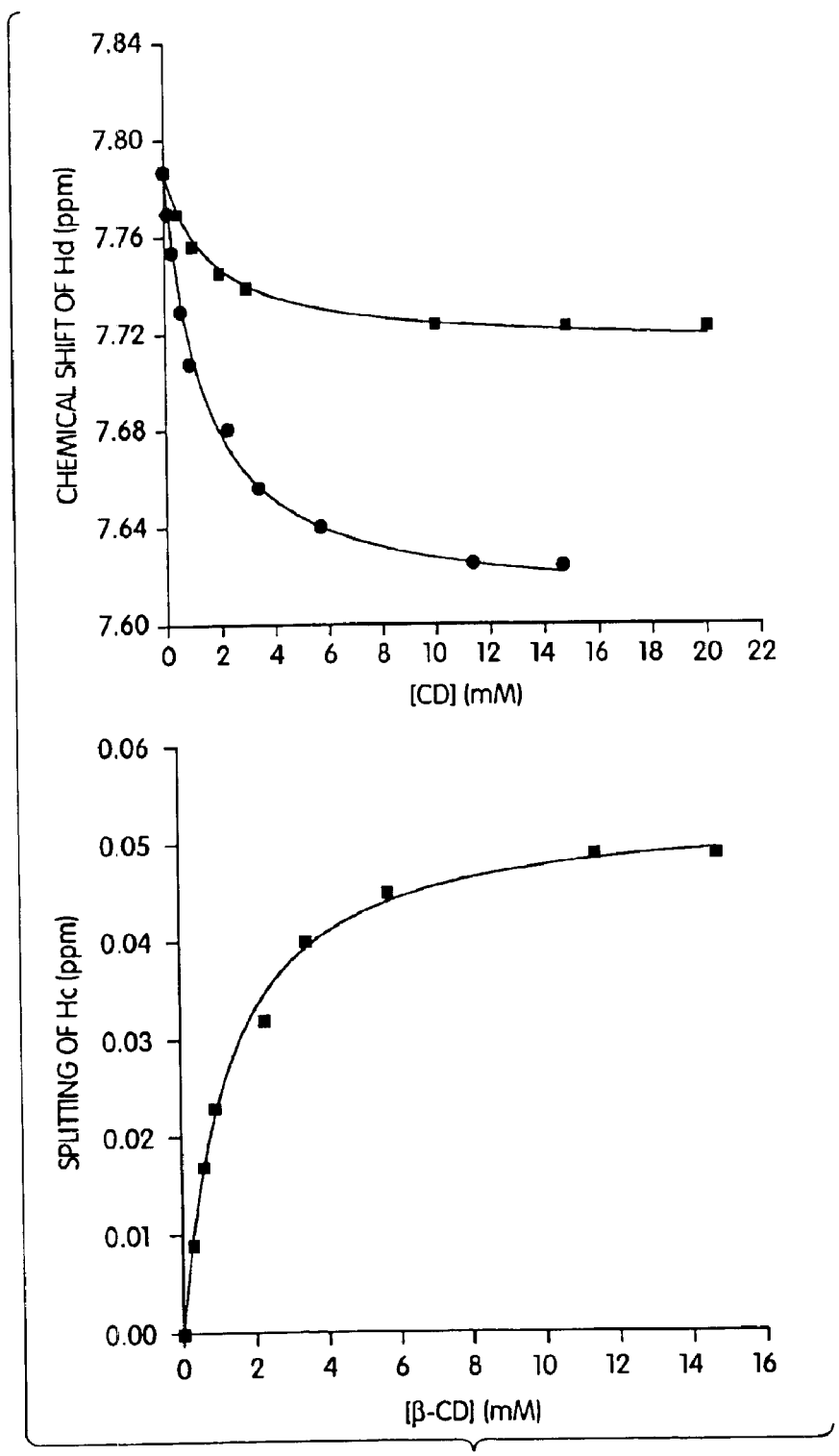
FIG. 5. Nonlinear curve fitting of (A) chemical shift of Hd in β-lap ([β-lap]=0.123 mM) as a function of HPβ-CD (■) and β-CD (●) concentrations in $D_2O$; (B) Splitting of Hc as a function of β-CD concentrations in $D_2O$.

The upfield shift of Hd (not for other phenyl protons) and the splittings of Ha, Hb and Hc indicate that these changes are the result of inclusion complex formation but not due to the non-specific interaction between cyclodextrin and β-lap. Chemical shift changes of Hd (FIG. 5A) as a function of β-CD and HPβ-CD concentrations and the splitting of Hc (FIG. 5B) as a function of β-CD gave good fits with a 1:1 complex model as shown in Equation 2 (A. Botsi, K. Yannakopoulou, B. Perly and E. Hadjoudis, *J Org Chem.* 60: 4017–4023 (1995)). The association constants determined from these data are 774±52 $M^{-1}$ (Hd shift), 734±20 $M^{-1}$ (Hc splitting) for β-CD.β-lap inclusion complex, and 662±27 $M^{-1}$ (Hd shift) for HPβ-CD.β-lap inclusion complex.

Fluorescence Studies of β-lap Inclusion Complex

Figure 6A:
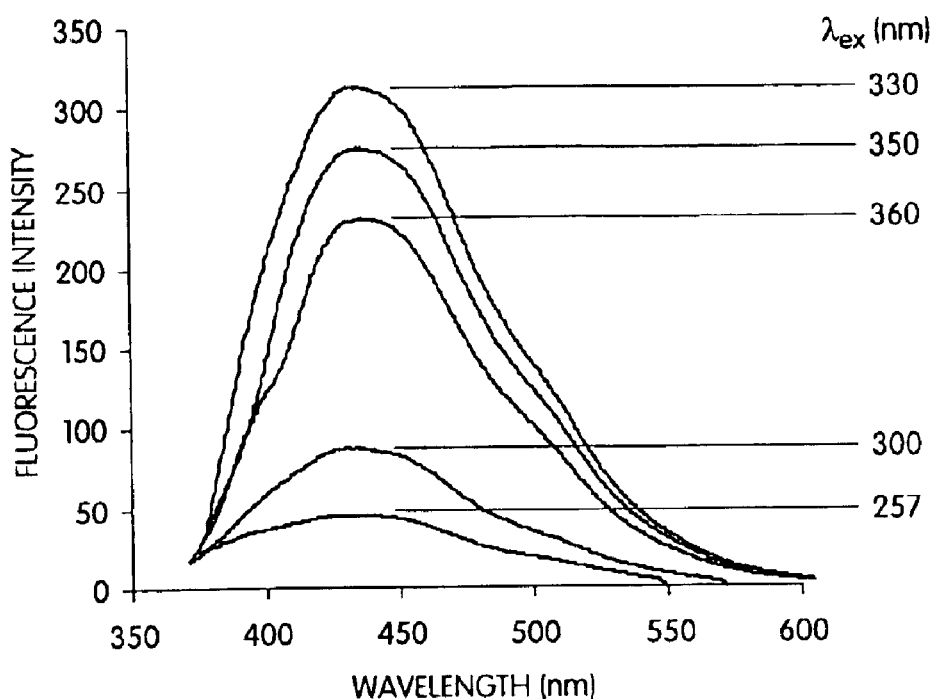
FIG. 6. A) Emission spectra of β-lap (61 μM) at different excitation wavelengths ranging from 257 to 360 nm. B) Emission spectra of β-lap (18 μM) in different HPβ-CD concentrations at 25° C. ($\lambda_{ex}$=330 nm).

In the course of this study, we discovered that β-lap was a fluorescent molecule, and we used fluorescence spectroscopy to further study the association of HPβ-CD.β-lap and β-CD.β-lap inclusion complexes. FIG. 6A shows a series of emission spectra of β-lap alone in PBS buffer at different excitation wavelengths ranging from 257 to 360 nm. These data showed that an excitation wavelength at 330 nm gave the highest emission intensity. For all the excitation wavelengths, the maximum emission wavelength was located at 436 nm. These experiments established the optimal spectroscopy conditions for β-lap complexation studies ($\lambda_{ex}$=330 nm, $\lambda_{em}$=436 nm).

Figure 6B:
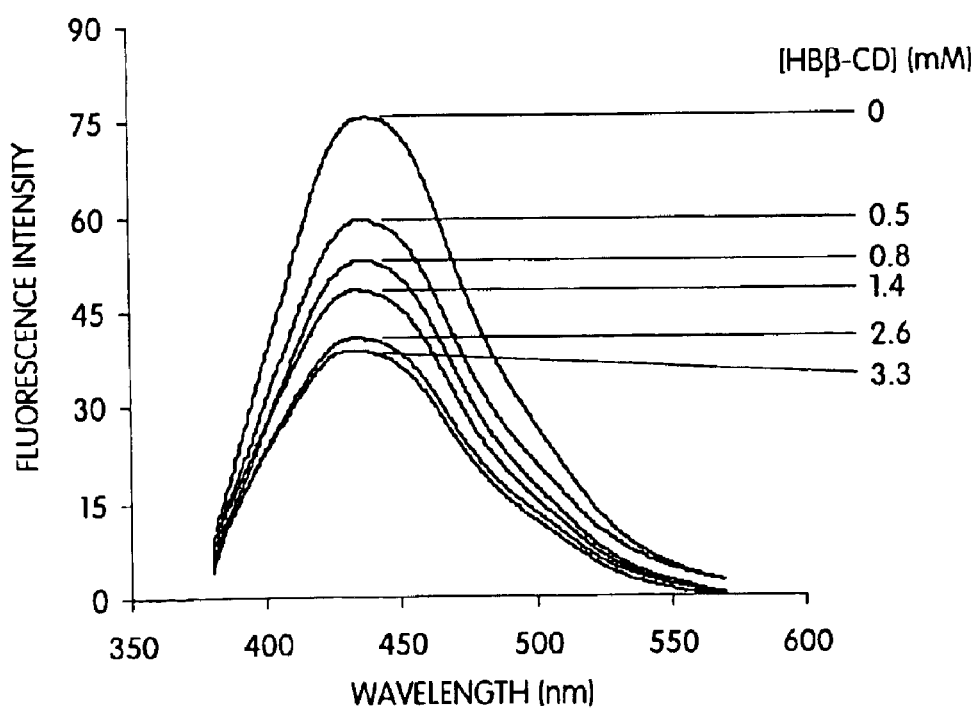

FIG. 6B shows the dependence of β-lap emission spectra as a function of HPβ-CD concentrations in PBS buffer. All the experiments were carried out at the same excitation wavelength ($\lambda_{ex}$=330 nm) and same β-lap concentration (18 μM). Results showed that the β-lap emission intensity decreased when the HPβ-CD concentration increased (FIG. 6B). In addition, there is a slight blue shift (~6 nm) of the maximum emission wavelength in solution containing HPβ-CD. The change in fluorescence intensity and maximum emission wavelength of guest β-lap compound by addition of cyclodextrins is another indication of the formation of inclusion complexes between these two compounds. Upon encapsulation inside the hydrophobic cavity of CD molecules, the β-lap compound encounters a different chemical environment compared to aqueous solution. Geometric restrictions due to space limitations in the CD cavity and reduced polarity due to the hydrophobic cavity of CD are found to alter the energetics and dynamics of the photophysical and photochemical processes of the guest molecule (V. Ramamurthy, D. F. Eaton. *Acc Chem Res.* 21:300–306 (1988)). The blue shift is consistent with the fact that β-lap experiences a less polar environment in the hydrophobic cavity of HPβ-CD.

Next, we determined the association constant for the formation of inclusion complex based on the fluorescence data. Emission intensity at 436 nm was used for these studies. Scatchard analysis by Equation 3 (E. E. Sideris, G. N. Valsami, M. A. Koupparis and P. E. Macheras, *Pharm Res.* 9(2): 1568–1574 (1992)) was used to determine the association constant ($K_c$) of the inclusion complex.

$$R/[CD]_f = n K_c - R K_c \qquad (3)$$

where $[CD]_f$ is the unbound (free) molar concentration of CD, n is the number of binding sites i.e. the stoichiometry of the complex and R is the molar fraction of β-lap bound to CD.

The values of $K_c$ are (1.10±0.06)×10$^3$ M$^{-1}$ (R$^2$=0.97) and (1.06±0.06)×10$^3$ M$^{-1}$ (R$^2$=0.98) for β-CD.β-lap and HPβ-CD.β-lap complexes, respectively. The numbers of binding sites (n) of β-CD.β-lap and HPβ-CD.β-lap inclusion complexes were found to be 1.04±0.02 and 1.01±0.02, respectively, which confirm the formation of 1:1 inclusion complexes. The values of $K_c$ from fluorescence measurement are consistent with those from phase solubility studies, but are higher than the data from NMR measurement. This different is most likely due to different solvents (e.g., PBS buffer were used in fluorescence and phase solubility studies, in comparison to D$_2$O in NMR studies).

In Vitro Cytotoxicity Studies in MCF-7 Cells

In order to evaluate the biological activity of β-lap when it forms an inclusion complex with cyclodextrin, initial cytotoxicity DNA assays using MCF-7 human breast cancer cells were performed. Previous studies (J. J. Pink, S. M. Planshon, C. Tagliarino, S. M. Wuerzberger-Davis, M. E. Varnes, D. Siegel and D. A. Boothman. *J Biol Chem.* 275:5416–5424 (2000); S. M. Wuerzberger, J. J. Pink, S. M. Planchon, K. L. Byers, W. G. Bornmann and D. A. Boothman. *Cancer Res.* 58(9):1876–85 (1998); C. Tagliarino, J. J. Pink, G. R. Dubyak, A. L. Nieminen and D. A. Boothman.

Figure 7:
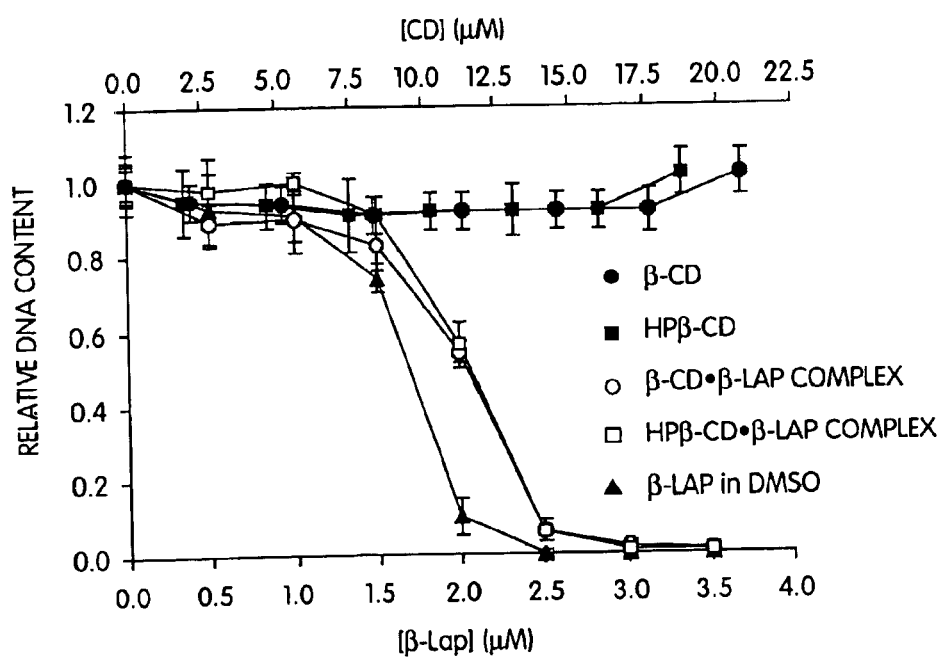
FIG. 7. Viability of log-phase MCF-7 cells exposed to β-lap in DMSO, HPβ-CD or β-CD inclusion complexes, as well as β-CD and HPβ-CD vehicles alone. For β-lap in DMSO and β-lap inclusion complexes, the bottom horizontal axis denotes the β-lap concentrations. The top horizontal axis denotes the cyclodextrin concentrations in β-lap inclusion complexes as well as for vehicles (β-CD and HPβ-CD) alone. Experiments were performed at least two times in triplicate to provide the standard deviation.

*J Biol Chem.* 276(22):19150–9 (2001)) have demonstrated that NQO1-expressing MCF-7 cells treated under these conditions tested not only growth inhibition, but the results can be equated to loss of survival using colony forming ability assays. Log-phase MCF-7 cells were exposed to different concentrations of β-lap in HPβ-CD inclusion complex, β-lap in β-CD inclusion complex, or with HPβ-CD and β-CD alone for four hours. Drugs were then removed and DNA content as a measure of cell survival was determined. β-Lap in DMSO was used as a positive control for comparison. FIG. 6 shows the viability of MCF-7 cells exposed to HPβ-CD.β-lap, β-CD.β-lap inclusion complexes, or with HPβ-CD and β-CD alone. The primary x-axis is the β-lap concentration used in this experiment and the secondary x-axis is the concentration of HPβ-CD and β-CD required to solubilize β-lap. Cell viability of MCF-7 cells was statistically identical for cells treated with vehicles (HPβ-CD, β-CD) alone or with PBS for 4 hours. These data showed that pure HPβ-CD (0 to 18.8 μM) and μ-CD (0 to 20.8 μM) alone showed no cytotoxicity or growth inhibition. β-lap in HPβ-CD and β-lap in β-CD inclusion complexes showed similar cytotoxic responses for the entire range of β-lap-equivalent doses (FIG. 7). Quantitatively, the drug potency was measured as $TD_{50}$, the toxic dose that kills 50% of the cell population. The $TD_{50}$ values of β-lap in HPβ-CD and β-CD inclusion complexes were found to be the same at 2.1 μM for a 4 h transient drug exposure. These values were slightly higher than that from β-lap in DMSO, whose $TD_{50}$ value is 1.7 μM.

In vivo Analyses of β-lap Toxicity

Figure 8:
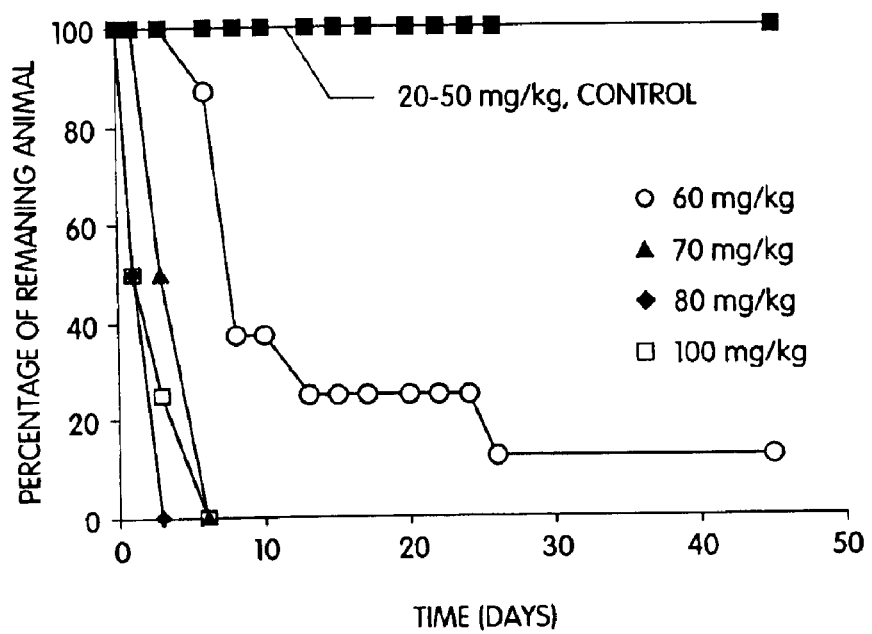
FIG. 8. Effect of varied doses of β-lap in HPβ-CD inclusion complex and HPβ-CD (control group injected with 5000 mg of HPβ-CD/kg) on the survival of C57Blk/6 mice. Animals were injected i.p. at day 1, 3, 6, 8, 10, 13, 15, 17, 20 and 22.

To evaluate the bioavailability of β-lap in CD inclusion complexes, C57Blk/6 mice were injected with increasing concentrations of β-lap in HPβ-CD inclusion complex three days per week for three weeks, and changes in weight and survival were recorded. Results showed no morbidity (decreases in weight loss) or lethality of mice for control group injected i.p. with vehicles alone, or for mice injected i.p with 20 to 50 mg/kg of β-lap in HPβ-CD inclusion complex. In contrast, mice injected i.p. with 70 to 100 mg/kg showed both morbidity and 100% lethality (FIG. 8). Finally, mice treated with 60 mg/kg β-lap in HPβ-CD inclusion complex i.p. resulted in significant morbidity (loss of >15% body weight in most animals) and lethality (7/8 animals died within 45 days of the treatment regimen). Consequently, the $LD_{50}$ (lethal dose that kills 50% of mice population) value of β-lap in HPβ-CD inclusion complex was estimated to be between 50–60 mg/kg in 18–20 gram C57Blk/6 mice. This was determined by considering that 50 mg/kg kills 0% of mice population and 60 mg/kg kills 85% of mice population in the course of this experiment. Interestingly, mice responded to doses above 50 mg/kg β-lap in HPβ-CD inclusion complex, but not with HPβ-CD vehicle alone, with unusual but temporary drug reactions. Within 15 mins post-i.p.-injection, mice were observed to have a shivering reflex and difficulty in breathing. These drug responses lasted approximately two hours, with mice exposed to 40–50 mg/kg recovering completely with essentially no weight loss noted overtime. In contrast, most mice exposed to >60 mg/kg exhibited similar drug responses that resulted in lethality. Preliminary autopsies with mice that ultimately died did not result in the detection of major damage to vital organs, and more detailed analyses of cause of death are ongoing. Our studies indicate a nearly 3-fold greater bioavailability of β-lap in vivo compared to previous animal studies using Cremophor as a vehicle for β-lap administration, where an $LD_{50}$ of >150 mg/kg was reported (C. J. Li, Y. Z. Li, A. V. Pinto and A. B. Pardee. *Proc Natl Acad Sci. USA.* 96(23):13369–74 (1999)).

Conclusion

Phase solubility studies of β-lap in complexation with α-CD, β-CD, HPβ-CD or γ-CD were carried out to overcome the problems of β-lap solubility and bioavailability. HPβ-CD demonstrated the maximum enhancement of β-lap solubility to 16.0 mg/ml or 66.0 mM, more than a 400-fold increase over β-lap solubility in water (0.04 mg/ml or 0.16 mM). The association constants of β-lap with cyclodextrins were determined by the phase solubility method, $^1$H NMR and fluorescence spectroscopy ($\lambda_{ex}$=330 nm, $\lambda_{em}$=436 nm). β-CD and HPβ-CD showed higher binding affinity ($K_c$=0.9–1.2×10$^3$ M$^{-1}$) to β-lap than α-CD (20 M$^{-1}$) and γ-CD (160 M$^{-1}$). Cytotoxicity assays indicated little differences in biological activity between β-lap in HPβ-CD or β-CD inclusion complexes, with nearly identical cell responses (cell death in induced apoptosis) and $TD_{50}$ values (2.1 μM). Finally, studies of morbidity and mortality in C57Blk/6 mice suggested a $LD_{50}$ between 50–60 mg/kg, with no morbidity or mortality following 20–50 mg/kg β-lap in HPβ-CD inclusion complex. Complexation of β-lap with HPβ-CD offers a major advancement in improvement of bioavailability of this very active anticancer agent.

Figure 9:
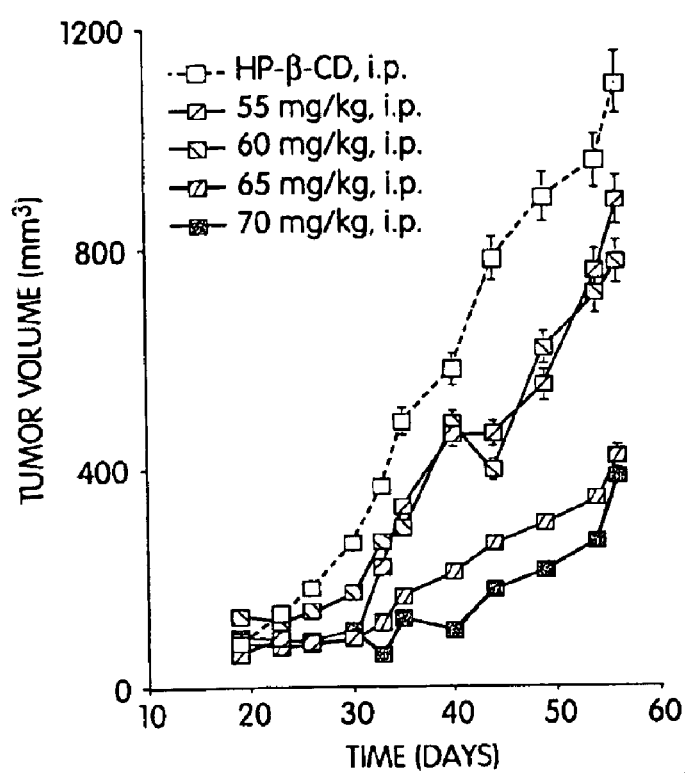
FIG. 9 shows responses of an implanted cell line to compositions of the present invention.

MDA_MB-468 NQO1+ Tumor (468) cells were injected into the right and left flanks of 18–20 gm athymic nude mice and tumors of 20–50 mm$^3$ volume were allowed to grow in 20–30 days. When tumor volumes reached 20–30 mm$^3$ (at day 26), mice were then treated (by intraperitoneal injection) every other day with the indicated doses (in mg/kg) of β-lap (55–70 mg/kg were tested). The maximum tolerated dose of β-lap in athymic nude mice was determined to be 80 mg/kg). Ten (10) β-lap doses were given every other day, and data are shown for only one cycle of β-lap treatment. Multiple cycles of treatments are now being tested, as are various dose regimen and scheduling protocols. For the 468 cell line, significant antitumor responses were observed with β-lap in a dose-responsive fashion (FIG. 9). Significant antitumor responses were observed with 65 and 70 mg/kg.

Figure 10A:
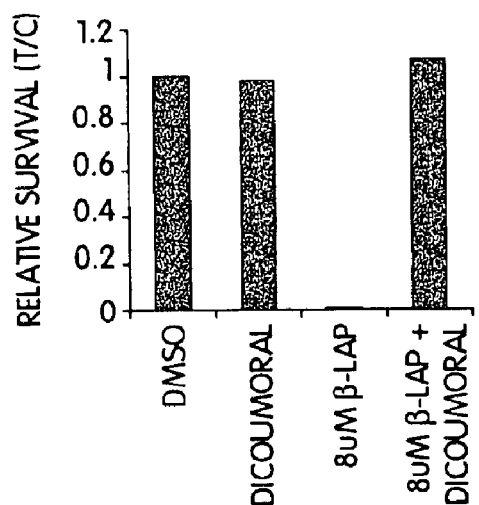
FIG. 10. NQO1-dependent apoptosis of A549 or CC-10 NSCLC cells by β-lap. Human A549 NSCLC cells were exposed to 8 μM β-lap, ±50 μM dicoumarol for 4 h, drugs were removed, and cells monitored for: survival (A); or Western blot analyses of PARP cleavage (B) as noted (Pink, J. J., Wuerzberger-Davis, S., Tagliarino, C., Planchon, S. M., Yang, X., Froelich, C. J., and Boothman, D. A. *Exp Cell Res,* 255: 144–155, 2000; Wuerzberger, S. M., Pink, J. J., Planchon, S. M., Byers, K. L., Bornmann, W. G., and Boothman, D. A. *Cancer Res,* 58: 1876–1885, 1998). Dicoumarol alone had no effect on cell growth (survival), but blocked β-lap-induced apoptotic PARP cleavage (see 60 kDa fragment in β-lap-treated cells, but not in cells treated with β-lap+dicoumarol). NQO1 levels remained unchanged and indicated equal loading (B). Similar results were found with CC-10 tumor cells, where dicoumarol blocked β-lap cytotoxicity (C).
Figure 10B:
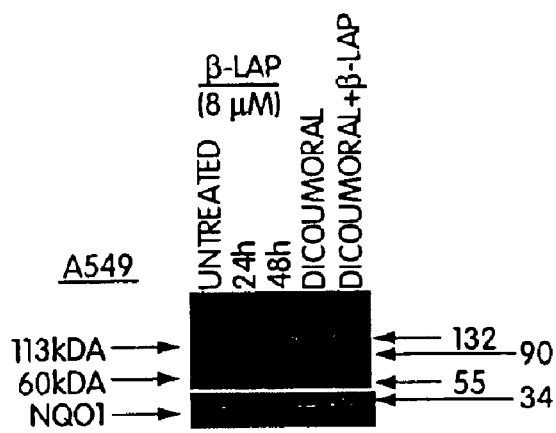
Figure 10C:
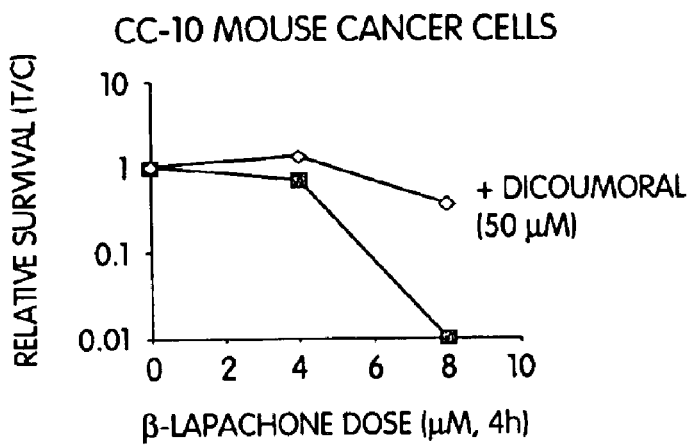

2. Lung Cancer Therapy

β-lap activity against human and mouse NSCLC. As expected for NQO1-expressing cell lines, β-lap treatment caused lethality and apoptosis in CC-10 or A549 NSCLC cells, which was blocked by 50 μM dicoumarol (FIG. 10). As observed with β-lap-treated NQO1-expressing human breast or prostate cancer cells (Pink, J. J., Planchon, S. M., Tagliarino, C., Varnes, M. E., Siegel, D., and Boothman, *J Biol Chem*, 275: 5416–5424, 2000; Planchon, S. M., Pink, J. J., Tagliarino, C., Bornmann, W. G., Varnes, M. E., and Boothman, D. A. *Experimental Cell Research,* 267: 95–106, 2001), atypical PARP cleavage was observed after β-lap exposure, and this apoptotic proteolysis was diminished by dicoumarol (FIG. 10B). PARP cleavage to a 60 kDa fragment and specific p53 proteolysis are diagnostic for β-lap-induced μ-calpain-mediated apoptosis. These data are consistent with our hypothesis that β-lap causes lethality in an NQO1-dependent manner to cause μ-calpain apoptotic cell death. Similar results were observed in mouse cells: Lewis lung carcinoma (LLC), CC-10 tumor cell lines derived from a spontaneous mouse CC-10 lung cancer model, and L1C2 cells expressed elevated levels of NQO1 compared to normal lung tissue (Table 2), and were extremely sensitive to β-lap (4 μM, 4 h). As expected, co-administration of dicoumarol prevented β-lap cytotoxicity in these cells.

Evaluation of NQO1 levels in normal mouse CC-10 lung v. CC-10 spontaneous tumors. In order to evaluate the efficacy of various vehicles carrying β-lap under various routes of administration, it is essential that the proposed CC-10 or LLC model systems mimic human disease with respect to NQO1 over-expression. To monitor NQO1 levels in vivo, CC-10 mice with spontaneous tumors were sacrificed and NSCLC as well as normal lung tissue was extracted and analyzed for NQO1 activities as previously described (Table 2). Human A549 and various mouse NSCLC cell lines were also evaluated (Table 2). As shown in Table 2, NQO1 levels were elevated in mouse CC-10 tissue 8-fold compared to adjacent normal tissue. Furthermore, mouse NSCLC cell lines were also elevated 12- to 21-fold above normal tissue. Interestingly, the A549 NSCLC cell line was also elevated over 1200-fold above normal mouse lung tissue (Table 2).

Table 2. Elevation of NQO1 in CC-10 tumor and NSCLC cell lines vs. normal tissue. NQO1 enzymatic activities were measured from spontaneous CC-10 lung tumor tissue v. adjacent normal lung tissue as described (Pink, J. J., Planchon, S. M., Tagliarino, C., Varnes, M. E., Siegel, D., and Boothman, D. A. *J Biol Chem*, 275: 5416–5424, 2000). In addition, mouse NSCLC cell lines, as well as the human A549 NSCLC cell line, were evaluated and compared to normal mouse tissue. Compared to normal mouse lung tissue, CC-10 tumor tissue NQO1 activity was elevated 8-fold.

| Cell Line/Tissue | NQO1 Activity ($\mu$M CytoC reduced/min/mg protein) | X-Fold Above Normal |
|---|---|---|
| Normal Lung (Mouse) | 4 | 1 |
| CC-10 Tumor (Mouse) | 34 | 8 |
| CC-10 Cell Line (Mouse) | 88 | 21 |
| L1C2 Cell Line (Mouse) | 54 | 12 |
| LLC Cell Line (Mouse) | 75 | 18 |
| A549 Cell Line (Human) | 5056 | 1200 |

Development of β-lap-loaded microspheres. Development of microspheres able to release β-lap under controlled conditions, and specifically within or near the lung, is a major goal of this grant. In initial experiments, the loading density of β-lap was controlled at 2% in polymer microspheres. Polymer microspheres were synthesized using a single-emulsion procedure (see Methods in Deng, X. M., Xiong, C. D., Cheng, L. M., Huang, H. H., and Xu, R. P. *Journal of applied polymer science*, 55: 1193–1196, 1995). Scanning electron microscopy (SEM) imaging of β-lap-loaded microspheres showed an average diameter of 3 $\mu$m of drug-carrying microspheres, a size that can be easily varied, and that should accumulate in the lungs of treated mice.

Figure 11:
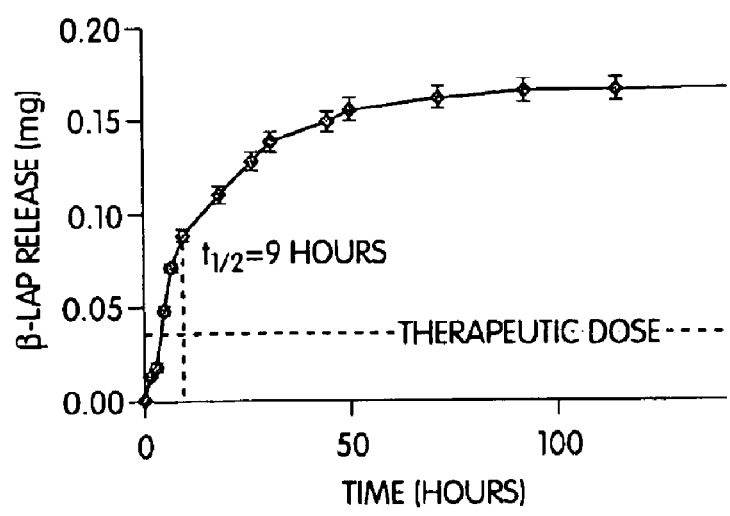
FIG. 11. Sustained release of β-lap from PLGA microspheres in PBS at 37° C. The loading density of β-lap in microspheres was 2.0±0.07%. The horizontal line at 0.035 mg is the predicted amount of β-lap to achieve 10 μM in a 3 cm diameter tumor.

Release studies. β-Lap release studies from polymer microspheres (n=3) were performed in PBS at 37° C. (FIG. 11). The time for 50% drug release of β-lap was 9 h, while nearly all (98%) was released in one week. Microsphere size can be varied (together with β-lap loading density) to control β-lap release kinetics from microspheres. The needed therapeutic dose of β-lap is calculated to be about 0.035 mg. This dose permits reaching the high-end of a therapeutic concentration of β-lap (10 $\mu$M) in a tumor with 3 cm diameter. Based on results in FIG. 11, microsphere systems can release therapeutic levels of β-lap in less than 5 h. These results indicate that desirable brief, but elevated, delivery of therapeutic doses of β-lap to primary and possibly metastatic tumor cells can be achieved with such microspheres.

Quantitative analyses of β-lap by HPLC-ESI-MS. To evaluate the in vivo pharmacokinetics of β-lap delivery from polymer microspheres, it was necessary to develop an accurate, highly sensitive, and quantitative method to measure the plasma concentration-time relationships and tissue distribution of β-lap. High pressure liquid chromatography-electrospray ionization-mass spectrometry (HPLC-ESI-MS) methodology for the quantitative analyses of β-lap was developed. The chromatographic medium was Ansys Metachem Polaris C18A (3$\mu$m particle diameter) contained inside a column of 0.46 cm i.d.×5 cm in length. The isocratic mobile phase was 25 mM ammonium formate+acetonitrile (v/v=50/50), at a flow rate of 0.5 mL/min. β-Lap was detected by selective reaction monitoring of the transition from 243 m/z (M+H)$^+$ to 187 m/z. Preliminary data showed superb sensitivity of detection under current experimental conditions. The lowest limit of quantification was $1.1\times10^{-14}$ mol of injected β-lap with a signal to noise ratio of 4:1. For a biological sample volume of 100 $\mu$L, this sensitivity permits detection of β-lap at 0.1 nM ($10^{-10}$ M). This methodology is suitable for quantitative analyses of β-lap levels in vivo. These data show the feasibility of HPLC-ESI-MS for highly sensitive and quantitative analyses for β-lap.

3. Treatment of Prostate Cancer

Fabrication of β-lap-loaded polymer millirods. The extremely low solubility of β-lap in water has greatly limited the clinical use of this compound. The development of drug-impregnated millirods, wherein β-lap release kinetics may be accurately permits the delivery of an efficacious form of therapy against human prostate tumors that commonly over-express the NQO1 oxidoreductase. The extinction coefficient for β-lap in water was determined to be $2.6\times10^4$ cm$^{-1}$M$^{-1}$ at 257 nm wavelength by UV-V is spectrophotometry. Solubility experiments were performed by immersing β-lap in PBS over a period of six days in an orbital shaker at 37° C. At the start of the experiment the drug suspension was sonicated for 20 seconds to facilitate the fast reach of solubility equilibrium. Samples were taken and filtered by 0.2 $\mu$m Millipore filters via syringe to remove non-dissolved drug particles and diluted to accommodate the UV-V is sensitive range before collecting absorbance data. Using the extinction coefficient, the solubility of β-lap in PBS buffer was $2.6\times10^{-4}$ M (0.05 mg/cc). This concentration is too low for i.v. administration in clinical applications. Preliminary experiments have demonstrated the feasibility of controlling the loading density of β-lap at 10% in PLGA polymer millirods. Polymer millirods were fabricated using a compression heat molding procedure as previously developed in our lab. (Halpert, B., Sheehan, E. and Schmalhorst, W. (1998) *Cancer* 82, 737–742.) Briefly, β-lap particles were mixed with polymer microspheres (4 $\mu$m) and various concentrations of glucose. Polymer microspheres were fabricated using a single emulsion procedure. Glucose particles were introduced as an excipient molecule at different loading densities (20%, 40%) to control the release kinetics of β-lap. The solid particle mixture was placed in a Teflon tube and heated to 90° C. at a compression pressure of 40 atm for 2 h. After compression heat molding, the polymer millirods were removed and cooled to room temperature for further characterization.

Figure 12:
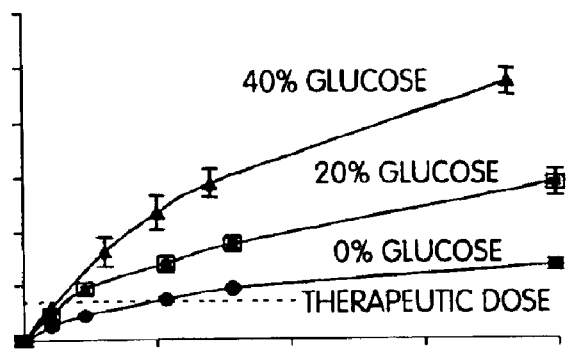
FIG. 12. Sustained release of β-lap from PLGA millirods in PBS at 37° C. The loading density of β-lap in millirods was 10%. The horizontal line at 0.035 mg represents the amount of β-lap to achieve a 10 μM concentration in a tumor of 3 cm in diameter.
Figure 13:
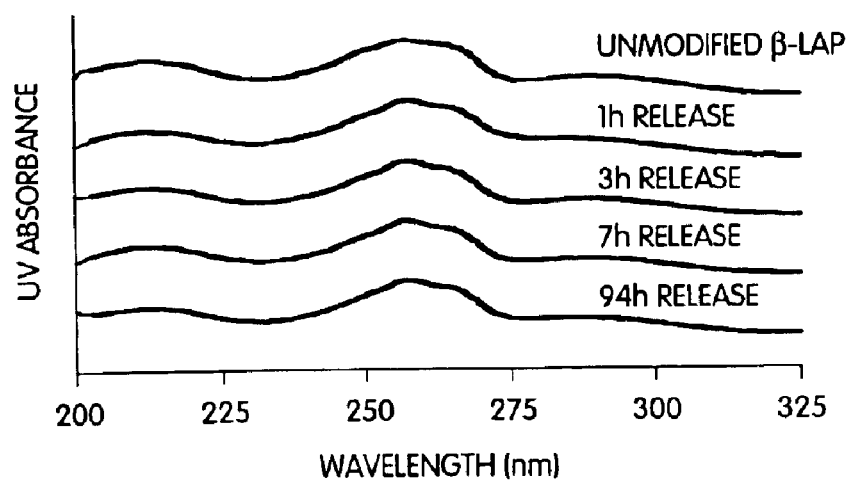
FIG. 13. Stacked UV-V is spectra of β-lap released at different time points. The similar signature peaks in UV-V is spectra (UV absorbance vs. Wavelength) suggest that the released β-lap maintains its structural integrity.

Release studies. Release studies of β-lap were performed in PBS at 37° C. FIG. 12 shows the release profiles of β-lap from polymer millirods. Addition of glucose effectively controlled the release rate of β-lap. Increasing the percentage of glucose led to faster release kinetics of β-lap from millirod polymers. For example, the amount of released β-lap increased from 0.05 mg in a millirod with 0% glucose to 0.15 mg in a millirod with 40% glucose after 7 h. The increased release rate was due to the dissolution of glucose particles from the polymer matrix that results in pores and channels facilitating release of β-lap. However, β-lap may not have been intact after polymer construction and release. FIG. 13 shows the stacked UV-V is spectra of β-lap released at different time points. Each spectrum was normalized to the peak UV absorbance and compared to that of the original sample. Identical UV-Vis spectra strongly suggest that structural integrity of the β-lap is maintained throughout the fabrication and controlled release studies. The necessary therapeutic dose of β-lap is 0.035 mg, a local concentration that would achieve 10 μM in a 3 cm diameter tumor. Based on results in FIG. 12, all millirods produced will release therapeutic levels of β-lap in less than 5 h.

TABLE 3

Dicoumarol blocks β-lap-induced apoptosis in NQO1+, but not NQO1−, isogenic LNCaP cells.

| Cell Line (+Pretreated Blocking Agent) | NQO1 Activity[1] | Apoptosis (%) After Drug Treatment | | | Campto-thecin (10 μM) |
|---|---|---|---|---|---|
| | | DMSO | β-Lapachone (10μM) | | |
| LNCaP | 3.0 ± 0.4 | 1.2 ± 0.7 | 28 | ±7 | 30 ± 5 |
| LNCaP + DC[2] | ND[3] | 0.91 ± 0.3 | 28 | ±3 | 33 ± 9 |
| LNCaP + DVED | 3.9 ± 0.3 | 0.62 ± 0.1 | 24 | ±6 | 10 ± 3 |
| DU-145 | 500 ± 48 | 0.08 ± 0.01 | 71 | ±13 | 30 ± 06 |
| DU-145 + DC | N–D | 0.10 ± 0.04 | 0.12 | ±0.03 | 43 ± 12 |
| DU-145 + DVED | 502 ± 41 | 0.11 ± 0.05 | 76 | ±12 | 10 ± 5 |
| PC-3 | 740 ± 100 | 0.06 ± 0.006 | 82 | ±15 | 23 ± 3 |
| PC-3 + DC | N–D | 0.04 ± 0.002 | 0.04 | ±0.005 | 22 ± 7 |
| PC-3 + DVED | 810 ± 130 | 0.03 ± 0.001 | 91 | ±12 | 6 ± 5 |

[1]NQO1 activity, nmols cytochrome C reduced/min/mg protein; + DC[2], 50 μM dicoumarol; N–D[3], no enzyme activity detected; TUNEL assays were used to monitor apoptosis, ± 50 μM dicoumarol. Drug treatments were for 4h, and TUNEL assays performed 48h post-treatment (Pink, J.J., Planchon, S.M., Tagliarino, C., Varnes, M.E. Siegel, D. and Boothman, D.A. (2000) J Biol Chem 275, 5416–5424). Experiments were performed at least three times in duplicate.

Evidence that NQO1 'bioactivates' β-lap in human CaP cells. Structural similarities between β-lap and other naphthoquinones suggested that NQO1 may be involved in its activation or detoxification. The IR-induction of NQO1 was consistent with this compound's ability to sensitize IR-treated cells. DU-145 or PC-3 cells were sensitive to β-lap in the absence of IR. LNCaP cells, which lack NQO1 expression and activity (Table 3) were resistant. Dicoumarol enhanced the survival of β-lap-treated DU-145 or PC-3 cells, increasing LD$_{90}$ values >3-fold for DU-145 and PC-3 cells, respectively; e.g., >95% lethality was noted in DU-145 cells after 4 μM β-lap, whereas the drug was ineffective (>95% survival) with 50 μM dicoumarol. Dicoumarol had no influence on the survival of β-lap-resistant LNCaP cells, and β-lap-treated LNCaP cells exhibited 3-fold less apoptosis than DU-145 or PC-3 cells (Table 3) (Planchon, S. M., Wuerzberger, S., Frydman, B., Witiak, D. T., Hutson, P., Church, D. R., Wilding, G. and Boothman, D. A. (1995) Cancer Res 55, 3706–3711). Changes in apoptosis (Table 3) mimicked lethality after drug exposure (X). In contrast, dicoumarol did not affect the lethality or apoptosis of LNCaP, DU-145 or PC-3 cells after camptothecin (CPT, a DNA Topoisomerase I poison) exposures (Wuerzberger, S. M., Pink, J. J., Planchon, S. M., Byers, K. L., Bornmann, W. G. and Boothman, D. A. (1998) Cancer Res 58, 1876–1885). DVED, an inhibitor of caspase-mediated apoptosis, blocked CPT-mediated apoptosis (Table 3), but not loss of survival (Pink, J. J., Wuerzberger-Davis, S., Tagliarino, C., Planchon, S. M., Yang, X., Froelich, C. J. and Boothman, D. A. (2000) Exp Cell Res 255, 144–155.

β-Lap-mediated proteolysis during apoptosis Cleavage of poly(ADP-ribosyl) polymerase (PARP) is a marker of apoptosis. Caspase-mediated cleavage results in an 89 kDa polypeptide by Western blot analyses. Human CaP cells treated with β-lap exhibited an atypical ~60 kDa PARP cleavage fragment. As expected, CPT induced a caspase-mediated 89 kDa PARP cleavage. Atypical PARP cleavage in CaP cells after β-lap exposure correlated well with apoptosis (Table 3) and clonogenic lethality, which was abrogated by dicoumarol. Atypical PARP cleavage was not affected by administration of 100 μM zVAD-fmk, a global caspase inhibitor, or DVED-fmk (Table 3). To date, no known caspases are activated in NQO1 expressing CaP or breast cancer cells after β-lap treatments (Tagliarino). Interestingly, lamin B cleavage (proteolysis observed during apoptosis) was noted in NQO1+ DU-145 cells after β-lap treatments. Cleavage of lamin B (60 kDa) to a 46 kDa polypeptide aids in nuclear matrix breakdown during apoptosis (Rao, L., Perez, D. and White, E. (1996) Journal of Cell Biology 135, 1441–1455). The pan-caspase inhibitor, 100 μM zVAD-fmk, did not inhibit lamin B cleavage after β-lap (Pink, J. J., Wuerzberger-Davis, S., Tagliarino, C., Planchon, S. M., Yang, X., Froelich, C. J. and Boothman, D. A. (2000) Exp Cell Res 255, 144–155). In mutant p53-expressing DU-145 cells, β-lap exposure resulted in p53 cleavage (40 and ~20 kDa) that were not inhibited by 100 μM zVAD-fmk. A similar p53 cleavage was described during μ-calpain-mediated apoptosis of neural cells (Kubbutat, M. H. and Vousden, K. H. (1997) Mol Cell Biol 17, 460–468; Shinohara, K., Tomioka, M., Nakano, H., Tone, S., Ito, H. and Kawashima, S. (1996) Biochem J 317, 385–388; Vanags, D. M., Orrenius, S. and Aguilar-Santelises, M. (1997) Br J Haematol 99, 824–831).

Figure 14A:
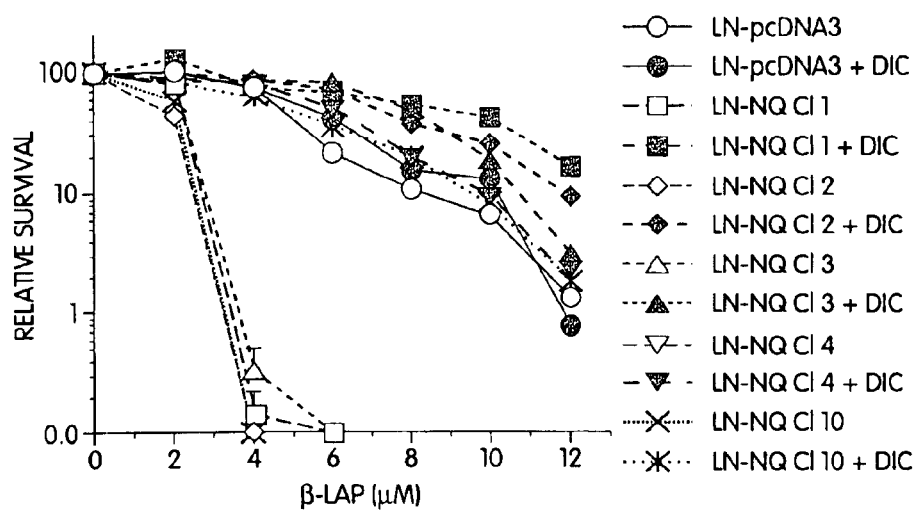
FIG. 14. NQO1 expression enhances β-lap, but decreases menadione, cytotoxicity. Left, NQO1-containing (LN-NQ Cl1-4, 10) and NQO1-deficient (LN-pcDNA3) LNCaP clones were treated with 4-h pulses of various doses of β-lap, ±50 μM dicoumarol. Colony forming ability assays (CFAs) were performed three times, each in triplicate. Open symbols: β-lap alone; Closed symbols: β-lap+50 μM dicoumarol. Right, a representative NQO1-transfected LNCaP clone (LN-NQ Cl 10) and one LNCaP vector alone clone (LN-pcDNA3) were treated with 4-h pulses of various doses of menadione and CFA assays were determined (Pink, J. J., Planchon, S. M., Tagliarino, C., Varnes, M. E., Siegel, D. and Boothman, D. A. (2000) *J Biol Chem* 275, 5416–5424).
Figure 14B:
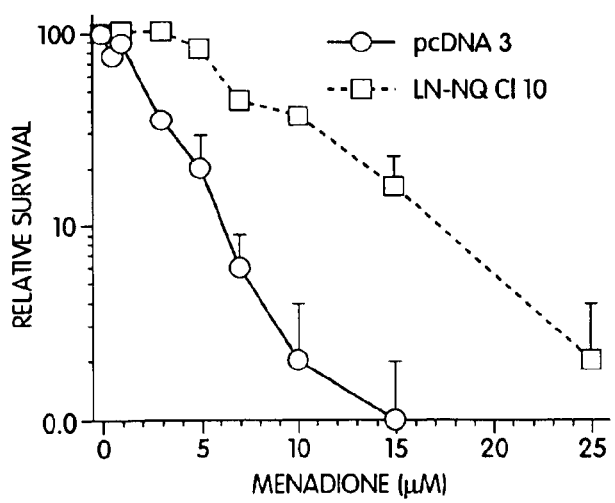

Expression of NQO1 sensitizes LNCaP cells to β-lap alone. LNCaP cells were transfected with either pcDNA3 empty vector or pcDNA3 containing full-length NQO1 cDNA. Five NQO1-containing (LN-NQ Cl 1-4, 10) and one vector alone (LN-pcDNA3) LNCaP clones were isolated (FIG. 14) and did not differ in P450 or b5R activities. In clonogenic assays, NQO1-deficient parental LNCaP cells were more resistant to β-lap than DU-145 or PC-3 cells. After transfection, NQO1-containing LNCaP clones were significantly more sensitive to β-lap than LNCaP cells containing pcDNA3 vector alone (FIG. 14), and as sensitive to β-lap as PC-3 or DU-145 cells. Dicoumarol administration returned NQO1-expressing LNCaP clones to the relative β-lap-resistant phenotype seen with LNCaP parental cells. Interestingly, NQO1-containing LN-NQ Cl 10 cells were resistant to menadione compared to NQO1-deficient LN-pcDNA3 cells. Dicoumarol reversed this resistance (FIG. 14B). NQO1-expressing LNCaP clone (LN-NQ Cl 1–4, 10) exposed to 10 μM β-lap resulted in significant apoptosis (i.e., 80–90%) compared to LNCaP vector alone clones, which showed <5% apoptosis. Dicoumarol prevented β-lap-induced apoptosis and atypical PARP cleavage in NQO1+ LNCaP clones. Similar results were shown in breast cancer cell lines.

NQO1 is an IR-inducible gene and is necessary for radiosensitization. We found that NQ01 was induced in U1-Mel cells, which are dramatically radiosensitized by β-lap. Treatment of U1-Mel cells with IR resulted in a dramatic increase in NQO1 transcript levels, cloned as xip3 (Boothman, D. A., Meyers, M., Fukunaga, N. and Lee, S. W. (1993) Proceedings of the National Academy of Science of the United States of America 90, 7200–7204). Peak levels of NQO1 were found 4–8 h post-IR. NQO1 levels were induced by as little as 1.0 Gy, a clinical dose of IR. Due to the limited availability of CaP cell lines expressing low NQO1 levels, studies on induction of NQO1 in CaP cells have been limited. All cell lines available to us have elevated endogenous NQO1 levels and were radiosensitized by β-lap. NQO1⁻ LNCaP cells were not sensitized.

Figure 15A:
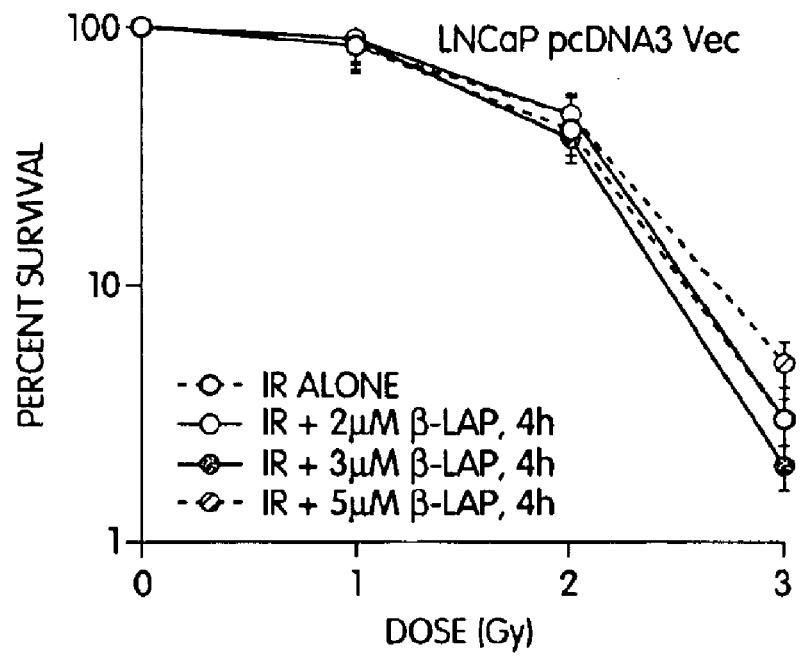
FIG. 15. NQO1 expression is required for radiosensitization of LNCaP cells by β-lap. NQO1⁻ LNCaP pcDNA3 vector alone and LNCaP NQO1⁺ clone 2 (NQCl2) cells were exposed to various IR doses, followed by various concentrations (in μM, 4-h) of β-lap. Changes in colony forming ability. In A, pcDNA3-vector alone cells were tested. In B, same as A, except that NQO1⁺ LNCaP cells were used.
Figure 15B:
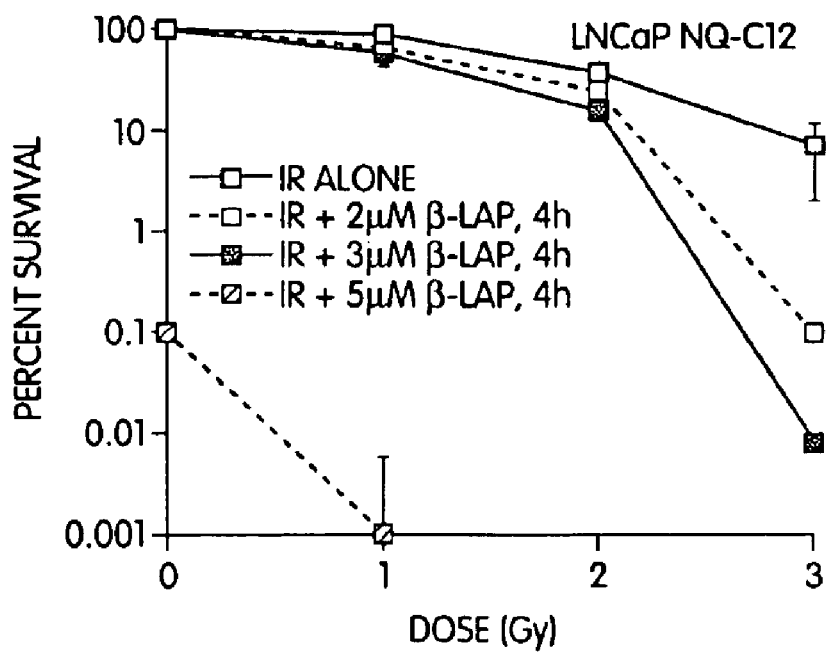
Figure 16:
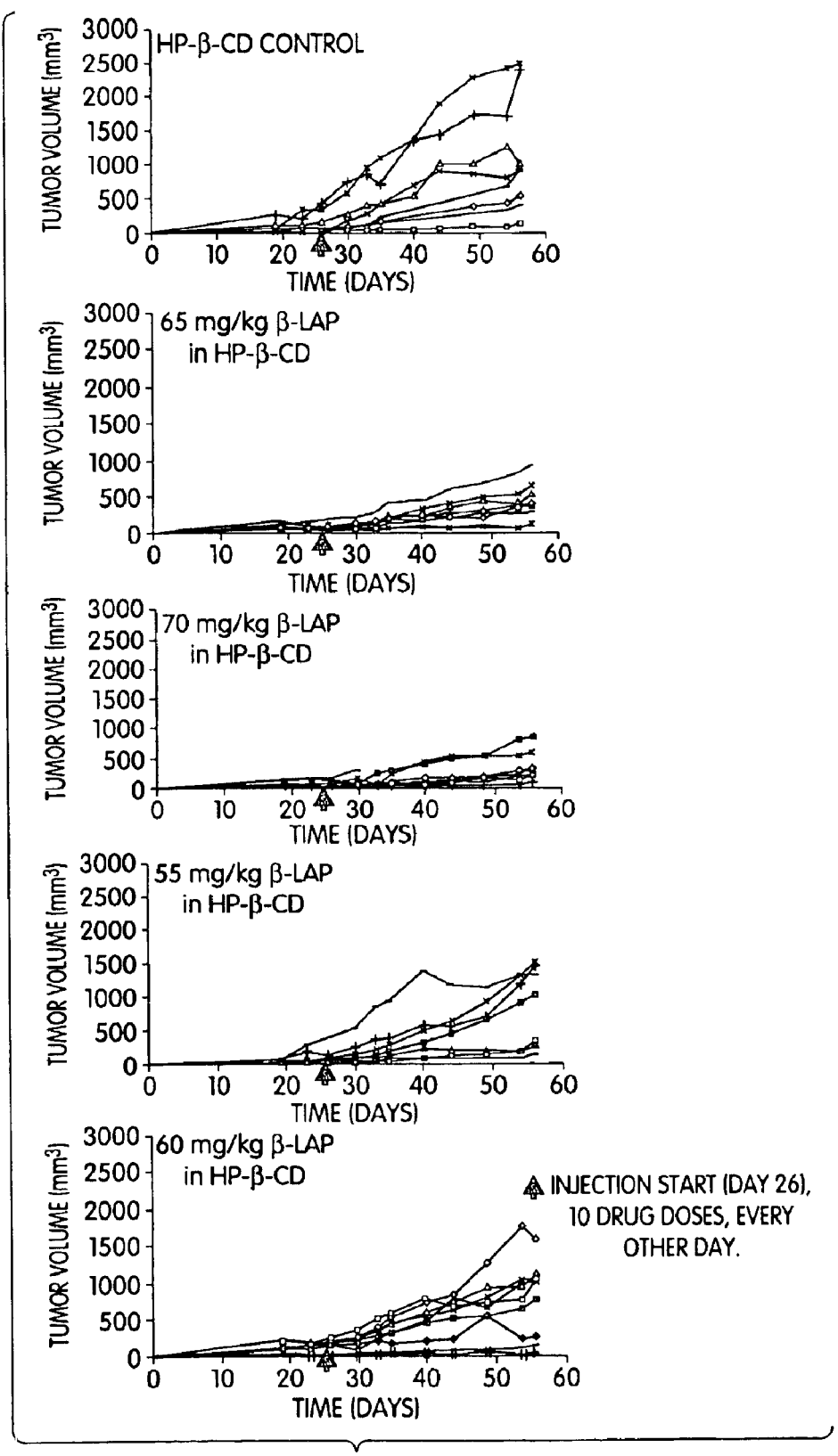
FIG. 16. β-Lap shows significant antitumor activity against MDA-MB-468 NQO1⁺ human xenografts. Athymic nude mice bearing 20 cm³ tumors were treated with the indicated mg/mk doses of β-lap i.p. every other day, beginning at day 26. Each line represents an individual tumor volume.

NQO1 is necessary for radiosensitization, but IR-induction is not required. To answer the question of whether NQO1 levels must be induced for β-lap radiosensitization, we examined NQO1⁺ LNCaP NQC12 v. NQO1⁻ LNCaP-pcDNA3 vector alone cells for differences in radiosensitization by various concentrations of β-lap, given 4 h post-IR (FIG. 15). Dose response clonogenic survival assays revealed two basic conclusions. First, only NQO1-expressing LNCaP cells were radiosensitized by β-lap treatments (FIG. 15B). Second, expression of NQO1 alone did not confer radioprotection of cells; it was possible that IR-induction of NQO1 would confer a survival advantage of cells following IR exposures. Finally, if the dose of β-lap was too high (i.e., 5 µM, FIG. 15B), radiosensitization was abolished due to the cytotoxicity of µ-lap alone. Similar results were found in breast cancer cell lines expressing or lacking NQO1. Thus, NQO1 expression was necessary for radiosensitization, and induction of the enzyme is not required for enhanced cell killing of IR-exposed cells by β-lap. This is important since NQO1-overexpressing CaP tumors should be sensitized by β-lap whether they induce, or already express, this enzyme; CaP tumors have 5- to 10-fold higher NQO1 levels.

β-lap bioavailability and antitumor activity. To show efficacy of β-lap in vivo, a systemic delivery system was developed for this water-insoluble drug. β-Lap complexes with β-hydroxypropyl-β-cyclodextrin (HP-β-CD) that dissolves the drug and makes it bioavailable. The toxicity of HP-β-CD.β-lap in 18–20 gm athymic nude mice was examined and the maximum tolerated dose (MTD) was ~75 mg/kg. This represents an ~3-fold greater bioavailability of β-lap in vivo than in previous studies using lipiodol, where an $LD_{50}$ of >150 mg/kg was noted for β-lap in C57/blk6 mice, and antitumor activity equal to taxol was noted with human ovarian xenografts. We tested the effects of β-lap administered i.p. in athymic nude mice bearing NQO1⁺ MDA-MB-468 (468) human breast cancer xenografts. Significant antitumor activity was noted in athymic mice bearing 468 xenografts when β-lap was administered at 55–70 mg/kg (FIG. 16).

REFERENCES

All publications and patents mentioned herein, are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A drug delivery composition selected from an implant, microparticles, and nanoparticles, wherein the composition comprises a lapachone incorporated in a biocompatible polymer having a molecular weight of about 2,000 or more daltons, and the lapachone has a structure of Formula I or II;

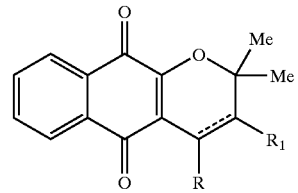

Formula I

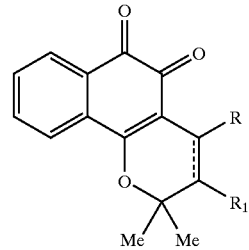

Formula II wherein R and $R_1$ each independantly represent H, Hydroxy, amino, amido, sulfhydryl, halogen, or substituted unsubstituted alkyl, alkenyl, heteroalkyl, carbocyclic aliphatic, carbocuclic aliphatic alkyl, aryl, aralkyl, heterocyclic aliphatic, heterocyclic aliphatic alkyl, heteroaryl, heteroaralkyl, or alkoxy,
or a pharmaceutically acceptable salt thereof.

2. The composition of claim 1, wherein the lapachone admixed with the polymer.

3. The composition of claim 1, wherein the composition is an implant.

4. The composition of claim 3, wherein the implant is a millirod dimensioned to position two radiation seeds at a predetermined distance from one another.

5. The composition of claim 1, wherein the composition is provided as microparticles.

6. The composition of claim 1, wherein the composition is provided as nanoparticles.

7. The composition of claim 1, further comprising hydroxypropyl β-cyclodextrin, wherein the lapachone is provided as an inclusion complex with hydroxypropyl β-cyclodextrin.

8. The composition of claim 1, wherein the lapachone is β-lapachone.

9. The composition of claim 1, wherein the polymer is biodegradable.

10. The composition of claim 1, wherein the polymer comprises one or more of poly(lactic-co-glycolic acid) (PLGA), poly(lactic acid) (PLA), polyethylene glycol (PEG), polysebacic acid (PSA), or a polyanhydride.

11. A method of inhibiting proliferation of a cancerous cell in a patient, comprising administering to the patient the drug delivery composition of claim 1.

12. The method of claim 11, wherein the cell overexpresses NQO1.

13. The method of claim 12, wherein the cell is a lung cancer cell, a breast cancer cell, or a prostate cancer cell.

14. The method of claim 13, wherein the cell is a non-small cell lung cancer cell.

15. The method of claim 14, wherein the composition is delivered to the patient by inhalation of microspheres comprising a lapachone and a biocompatible polymer.

16. The method of claim 11, wherein the cell is a prostate cancer cell and the composition is delivered to the patient by implanting radioactive seeds spaced apart by at least one polymeric millirod comprising a lapachone and a biocompatible polymer.

17. A composition of claim 1, wherein a therapeutic agent, a diagnostic agent, an imaging agent, or an adjuvant is also incorporated in the polymer.

18. A kit comprising a lapachone or a prodrug thereof, a β-cyclodextrin, and instructions for combining the lapachone and β-cyclodextrin to form a complex and administering the complex to a patient.

19. A kit comprising at least two radioactive seeds, at least one millirod according to claim 4, and instructions for administering the radioactive seeds and millirod to a patient.

20. A composition of claim 1, wherein the biocompatible polymer has a molecular weight of about 2,000 to about 1,000,000 daltons.

* * * * *

UNITED STATES PATENT AND TRADEMARK OFFICE
CERTIFICATE OF CORRECTION

PATENT NO. : 6,890,950 B2
DATED : May 10, 2005
INVENTOR(S) : Boothman et al.

It is certified that error appears in the above-identified patent and that said Letters Patent is hereby corrected as shown below:

Column 46,
Line 21, please replace "Hydroxy" with -- hydroxy --
Line 24, please delete "bocuclic" with -- bocyclic --
Line 41, please add -- the -- after "complex with"

Signed and Sealed this

Ninth Day of August, 2005

JON W. DUDAS
*Director of the United States Patent and Trademark Office*